US008642602B2

(12) United States Patent
Mann et al.

(10) Patent No.: US 8,642,602 B2
(45) Date of Patent: Feb. 4, 2014

(54) METHOD OF INHIBITING FIBROGENESIS AND TREATING FIBROTIC DISEASE

(75) Inventors: Jelena Mann, Newcastle Upon Tyne (GB); Chung K. Chu, Stratham, GA (US); Derek A. Mann, Newcastle Upon Tyne (GB)

(73) Assignees: University of Georgia Research Foundation, Inc., Athens, GA (US); University of Newcastle Upon Tyne, New Castle Upon Tyne (GB)

( * ) Notice: Subject to any disclaimer, the term of this patent is extended or adjusted under 35 U.S.C. 154(b) by 0 days.

(21) Appl. No.: 13/146,165

(22) PCT Filed: Feb. 2, 2010

(86) PCT No.: PCT/US2010/000283
§ 371 (c)(1),
(2), (4) Date: Sep. 26, 2011

(87) PCT Pub. No.: WO2010/090723
PCT Pub. Date: Aug. 12, 2010

(65) Prior Publication Data
US 2012/0014962 A1    Jan. 19, 2012

Related U.S. Application Data

(60) Provisional application No. 61/206,774, filed on Feb. 4, 2009, provisional application No. 61/277,284, filed on Sep. 22, 2009.

(51) Int. Cl.
*A61K 31/519* (2006.01)
*A61K 31/415* (2006.01)
*A61K 31/335* (2006.01)

(52) U.S. Cl.
USPC ........ 514/258.1; 514/393; 514/394; 514/463; 514/893

(58) Field of Classification Search
USPC .......... 514/86, 88, 274, 258.1, 393, 394, 463, 514/893
See application file for complete search history.

(56) References Cited

U.S. PATENT DOCUMENTS

| | | | |
|---|---|---|---|
| 6,020,320 A | 2/2000 | Von Borstel | |
| 6,670,342 B2 * | 12/2003 | Casey et al. | 514/86 |
| 7,511,027 B2 * | 3/2009 | Casey et al. | 514/86 |
| 2003/0225037 A1 | 12/2003 | Storer | |

FOREIGN PATENT DOCUMENTS

WO    2007047793 A2    4/2007

OTHER PUBLICATIONS

Dalgic et al., "Liver Transplantation and Tacrolimus Monotherapy for Hepatocellular Carcinoma with Expanded Criteria", Transplantation Proceedings, vol. 37, No. 7, pp. 3154-3156 (2005).*

Yavrom S, Chen L, Xiong S, Wang J, Rippe RA, Tsukamoto H. Peroxisome proliferator-activated receptor gamma suppresses proximal alpha1(I) collagen promoter via inhibition of p300-facilitated NF-I binding to DNA in hepatic stellate cells. J Biol Chem. Dec. 9, 2005;280(49):40650-9.

Klein ME, Lioy DT, Ma L, Impey S, Mandel G, Goodman RH. Homeostatic regulation of MeCP2 expression by a CREB-induced microRNA. Nat Neurosci. Dec. 2007;10(12):1513-4.

Fuks F, Hurd PJ, Deplus R, Kouzarides T. The DNA methyltransferases associate with HP1 and the SUV39H1 histone methyltransferase. Nucleic Acids Res. May 1, 2003;31(9):2305-12.

Kirmizis A, Bartley SM, Kuzmichev A, Margueron R, Reinberg D, Green R, Farnham PJ. Silencing of human polycomb target genes is associated with methylation of histone H3 Lys 27.Genes Dev. Jul. 1, 2004;18(13):1592-605.

Schotta, G., Lachner, M., Peters, A. H., and Jenuwein, T. ; The Indexing Potential of Histone Lysine Methylation; Novartis Found. Symp. (2004) , 259, 22-47, 163-169.

Houglum K, Lee KS, Chojkier M. Proliferation of hepatic stellate cells is inhibited by phosphorylation of CREB on serine 133. J Clin Invest. Mar. 15, 1997;99(6):1322-8.

Mann J, Oakley F, Akiboye F, Elsharkawy A, Thorne AW, Mann DA. Regulation of myofibroblast transdifferentiation by DNA methylation and MeCP2: implications for wound healing and fibrogenesis. Cell Death Differ. Feb. 2007;14 (2):275-85.

O'Neill LP, Turner BM. Immunoprecipitation of native chromatin: NChIP. Methods. Sep. 2003;31(1):76-82.

Wright MC, Issa R, Smart DE, Trim N, Murray GI, Primrose JN, Arthur MJ, Iredale JP, Mann DA. Gliotoxin stimulates the apoptosis of human and rat hepatic stellate cells and enhances the resolution of liver fibrosis in rats. Gastroenterology. Sep. 2001;121(3):685-98.

Oakley F, Mann J, Nailard S, Smart DE, Mungalsingh N, Constandinou C, Ali S, Wilson SJ, Millward-Sadler H, Iredale JP, Mann DA. Nuclear factor-kappaBl (p50) limits the inflammatory and fibrogenic responses to chronic injury. Am J Pathol. Mar. 2005;166(3):695-708.

De Minicis S, Seki E, Uchinami H, Kluwe J, Zhang Y, Brenner DA, Schwabe RF. Gene expression profiles during hepatic stellate cell activation in culture and in vivo. Gastroenterology. May 2007;132(5):1937-46.

Hui AY, Friedman SL. Molecular basis of hepatic fibrosis. Expert Rev Mol Med. Feb. 14, 2003;5(5):1-23. Review.

Tsukamoto H, She H, Hazra S, Cheng J, Miyahara T. Anti-adipogenic regulation underlies hepatic stellate cell transdifferentiation. J Gastroenterol Hepatol. Oct. 2006;21 Suppl 3:S102-5. Review.

She H, Xiong S, Hazra S, Tsukamoto H. Adipogenic transcriptional regulation of hepatic stellate cells. J Biol Chem. Feb. 11, 2005;280(6):4959-67.

(Continued)

*Primary Examiner* — Kevin E Weddington
(74) *Attorney, Agent, or Firm* — Henry D. Coleman; R. Neil Sudol

(57) ABSTRACT

The present invention relates to the discovery of an epigenetic relay pathway that controls hepatic stellate cell activation and the wound-healing response in fibrogenesis, including fibrogenesis of the injured liver. Methods of inhibiting fibrogenesis, including liver fibrogenesis and secondary disease states and conditions thereof, and in treating liver damage, including cirrhosis of the liver (which may be caused by viruses or chemicals, including alcohol), are aspects of the present invention. The methods utilize certain nucleoside compounds and/or antibodies which are optionally conjugated. Pharmaceutical compositions represent additional aspects of the invention.

18 Claims, 12 Drawing Sheets

(56) References Cited

OTHER PUBLICATIONS

Friedman SL. Mechanisms of hepatic fibrogenesis. Gastroenterology. May 2008;134(6):1655-69. Review.

Iredale JP, Benyon RC, Arthur MJ, Ferris WF, Alcolado R, Winwood PJ, Clark N, Murphy G. Tissue inhibitor of metalloproteinase-1 messenger RNA expression is enhanced relative to interstitial collagenase messenger RNA in experimental liver injury and fibrosis. Hepatology. Jul. 1996;24(1):176-84.

Klemm DJ, Leitner JW, Watson P, Nesterova A, Reusch JE, Goalstone ML, Draznin B.; Insulin-Induced Adipocyte Differentiation; J Biol Chem. Jul. 27, 2001;276(30):28430-5.

Hazra S, Xiong S, Wang J, Rippe RA, Krishna V, Chatterjee K, Tsukamoto H. Peroxisome proliferator-activated receptor gamma induces a phenotypic switch from activated to quiescent hepatic stellate cells. J Biol Chem. Mar. 19, 2004;279(12):11392-401.

Cheutin T, McNairn AJ, Jenuwein T, Gilbert DM, Singh PB, Misteli T. Maintenance of stable heterochromatin domains by dynamic HP1 binding. Science. Jan. 31, 2003;299(5607):721-5.

Francis NJ, Kingston RE, Woodcock CL. Chromatin compaction by a polycomb group protein complex. Science. Nov. 26, 2004;306(5701):1574-7.

Chahrour M, Jung SY, Shaw C, Zhou X, Wong ST, Qin J, Zoghbi HY. MeCP2, a key contributor to neurological disease, activates and represses transcription. Science. May 30, 2008;320(5880):1224-9.

Friedman SL. Hepatic stellate cells: protean, multifunctional, and enigmatic cells of the liver. Physiol Rev. Jan. 2008;88 (1):125-72. Review.

Friedman S et al. Mechanisms of Disease: mechanisms of hepatic fibrosis and therapeutic implication. Nat. Clin. Pract. Gastroenterol. Hepatol. 2004, 1:98-105.

Mann J et al. Regulation of myofibroblast transdifferentiation by DNA methylation and MeCP2: implications for wound healing and fibrogenesis. Cell Death and Differentiation. 2007, 14:275-285.

Vire E et al. MeCP2 targets the polycomb group protoin EZH2 to promoters. IN:The Belgian Society for Cell and Developmental Biology Spring meeting 2007, "Chromatin dynamics and epigenetics." Mar. 10, 2007 Abstract poster 45, Organized by Winkler, R et al. Liege, Belgium.

* cited by examiner

CpG island

Start at -372 from the start of A1 exon, extends over the A1 exon and 626bp into intron 1.
%CG=59.8, length of the island is 1412bp.

Morphology at day 7

Control

Compound 1

Compound 2

Compound 3
DZNep

Compound 4

Compound 9

METHOD OF INHIBITING FIBROGENESIS AND TREATING FIBROTIC DISEASE

This application claims the benefit of priority of U.S. provisional application Ser. Nos. U.S. 61/206,774, filed Feb. 4, 2009, entitled "Methods of Inhibiting Liver Fibrogenesis and Treating Liver Damage, Including Cirrhosis of the Liver" and 61/277,284, filed Sep. 22, 2009, entitled "Methods of Inhibiting Fibrogenesis and Treating Fibrotic Disease", both of which applications are incorporated by reference in their entirety herein.

RELATED APPLICATIONS AND GRANT SUPPORT

This application was supported by NIAAA/NIH grants, R21AA016682, R24AA012885, and P50AA11999. Consequently, the government retains certain rights in the invention.

FIELD OF THE INVENTION

The present invention relates to the discovery of an epigenetic relay pathway that controls hepatic stellate cell activation and the wound-healing response of the injured liver. Methods of inhibiting fibrogenesis in a patient, including liver fibrogenesis and treating liver damage, including cirrhosis of the liver (which may be caused by viruses or chemicals, including alcohol) as well as fibrotic disease states and conditions including fibrotic liver diseases and conditions, are further aspects of the present invention.

BACKGROUND AND BRIEF DESCRIPTION OF THE INVENTION

The liver neutralises microbial infections and detoxifies xenobiotics. However, exposure to these agents results in liver cell damage which necessitates a rapid and efficient wound-healing response. Central to this wound-healing is the local production of scar-forming myofibroblasts. A rapid response mechanism for generating hepatic myofibroblasts is the transdifferentiation of resident quiescent retinoid-storing hepatic stellate cells (Friedman S L 2008). Myofibroblast transdifferentiation (MTD) also occurs with pancreatic stellate cells and renal mesangial cells in the injured pancreas and kidney respectively (Ornery et al JCI-2007, Simonson M S 2007), suggesting biological conservation of the process. MTD is associated with global changes in gene transcription required for the cell to adopt the pro-inflammatory and pro-fibrogenic characteristics of the myofibroblast (Smart and Mann 2002). Regulation of MTD-associated gene expression is poorly understood but must be under strict control to prevent inappropriate wound healing (or fibrosis). Here we describe a novel epigenetic relay that is initiated by loss of expression of microRNA miR132 and which culminates in transcriptional silencing of PPARγ, a master negative regulator of MTD of hepatic stellate cells (She H et al 2005, Tsukamoto H et al 2006). We further describe two key components of the relay pathway, MeCP2 and EZH2, as critical regulators of hepatic wound-healing.

The present invention relates to the use of a compound according to the chemical structure Ia:

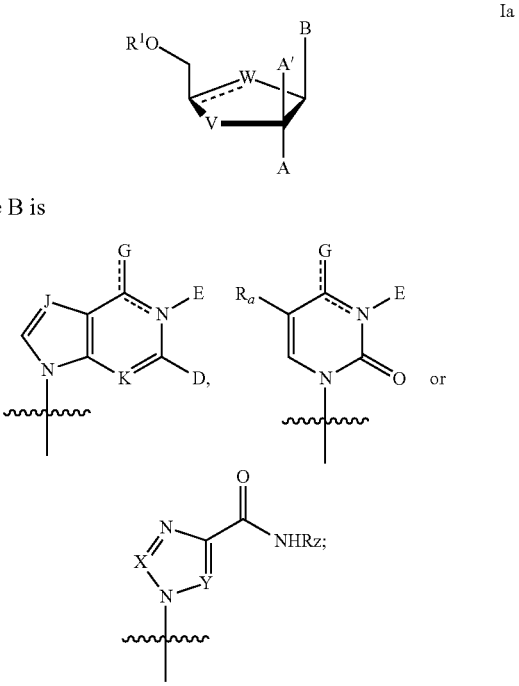

Where B is

W is C—H, O or S (preferably C—H or O, more preferably C—H) such that the bond between W and the adjacent carbon atom is a double bond when W is C—H and a single bond when W is O or S;
V is C-A", O or S, preferably with the proviso that when V is O or S, W is O or S (preferably, both V and W are O);
A is H, $OR^2$ or halogen (F, Cl, Br, I, preferably F or Br, more preferably F);
A' is H, $OR^2$ or halogen (F, Cl, Br, I, preferably F or Br, more preferably F);
A" is H or $OR^1$, with the proviso that when A' is $OR^2$, A is H; and when A is $OR^2$, A' is H;
X is C—$R^3$ or N;
Y is C—$R^3$ or N; preferably X or Y is N and X and Y are not both simultaneously N;
Rz is H or a $C_1$-$C_3$ alkyl group, optionally substituted with OH (preferably H);
$R^3$ is H, a halogen or $C_1$-$C_3$ alkyl;
D is H, a halogen (preferably F, Cl or Br) or $NR^{1a}R^2$;
E is absent (when G is $NHR^2$) or H (when G is O);
G is O or $NR^{1a}R^2$;
J is N or C—$R^4$;
K is N or C—H;
$R^4$ is H, halogen (F, Cl, Br, I), CN, —C(=O)$NH_2$, $NH_2$, $NO_2$, —C=C—H (cis or trans) or —C≡C—H;
$R_a$ is H or $CH_3$;
Each $R^1$ is independently H, an acyl group, a $C_1$-$C_{20}$ alkyl or ether group, an amino acid (D or L), a phosphate, diphosphate, triphosphate, phosphodiester group;
Each $R^{1a}$ and $R^2$ is independently H, an acyl group, a $C_1$-$C_{20}$ alkyl or ether group, an amino acid (D or L) or together $R^{1a}$ and $R^2$ form a $C_3$-$C_7$ cycloalkyl group; and
pharmaceutically acceptable salts, solvates or polymorphs thereof to treat and/or inhibit fibrogenesis in a patient or subject especially including fibrotic disease and/or conditions, including liver fibrosis and/or cirrhosis of the liver, in particular fibrosis and cirrhosis which may be caused by viruses, chemical and/or drugs.

Certain alternative embodiments for use in treating and/or inhibiting fibrogenesis, including fibrotic disease and/or conditions as otherwise described herein include compounds wherein W and V are both O and wherein B, A, A' and $R^1$ are the same as described for formula Ia above.

Alternative preferred compounds for use in treating and/or inhibiting fibrogenesis, including fibrotic disease and/or conditions as otherwise described herein include compounds according to the chemical structure Ib (W is a C—H):

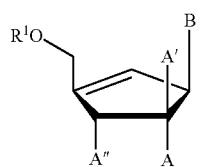

Ib

Wherein B, A, A', A" and $R^1$ are the same as described for formula Ia above.

Fibrotic diseases which may be treated according to the present invention include, for example, liver fibrosis (alcoholic, viral, autoimmune, metabolic and hereditary chronic disease), renal fibrosis (e.g., resulting from chronic inflammation, infections or type II diabetes), lung fibrosis (idiopathic or resulting from environmental insults including toxic particles, sarcoidosis, asbestosis, hypersensitivity pneumonitis, bacterial infections including tuberculosis, medicines, etc.), interstitial fibrosis, systemic scleroderma (autoimmune disease in which many organs become fibrotic), macular degeneration (fibrotic disease of the eye), pancreatic fibrosis (resulting from, for example, alcohol abuse and chronic inflammatory disease of the pancreas), fibrosis of the spleen (from sickle cell anemia, other blood disorders) cardiac fibrosis (resulting from infection, inflammation and hypertrophy), mediastinal fibrosis, myelofibrosis, endomyocardial fibrosis, retroperitoneal fibrosis, progressive massive fibrosis, nephrogenic systemic fibrosis, fibrotic complications of surgery, especially surgical implants, injection fibrosis and secondary conditions and disease states of fibrosis. Secondary conditions and disease states of fibrosis include for example, cirrhosis, diffuse parenchymal lung disease, post-vasectomy pain syndrome and rheumatoid arthritis, among others.

In certain preferred aspects of the present invention (especially including compounds according to formula Ib), A is OH, A' is H and A" is OH, J is N or $CR^4$, K is N or CH, X is N, Y is $CR^3$, E is absent and G is $NHR^2$. In other preferred embodiments, J is N, K is CH and G is O or $NHR^2$. In many preferred embodiments, $R^1$ and $R^2$ are both H. In certain preferred embodiments, $R^4$ is an acetylenic group.

In other embodiments, the preferred compound is

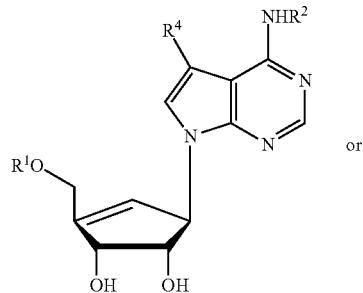 or

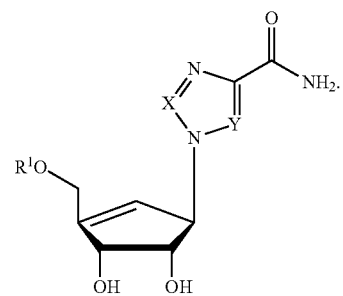

Where $R^1$, $R^2$, $R^4$, X and Y are the same as described above. Other preferred compounds may be readily gleaned from the description of the invention which follows.

In still other preferred embodiments, the compound is according to the chemical structure Ic hereinbelow:

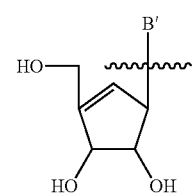

Ic

Where B' is

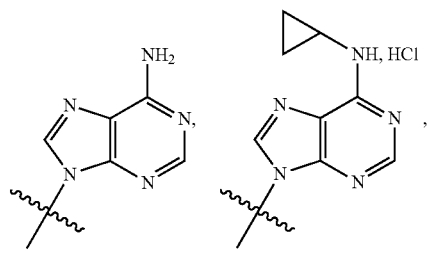

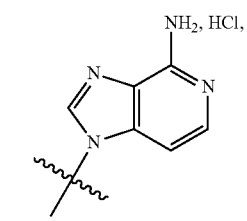

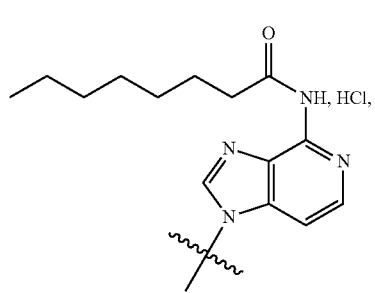

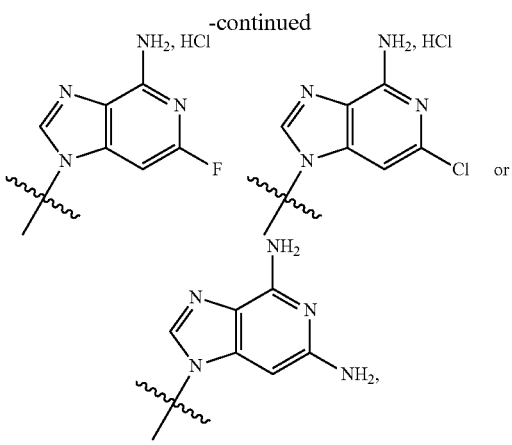

Or pharmaceutically acceptable salts, solvates or polymorphs thereof.

In still other preferred embodiments compounds which may be used in the present invention include the following:

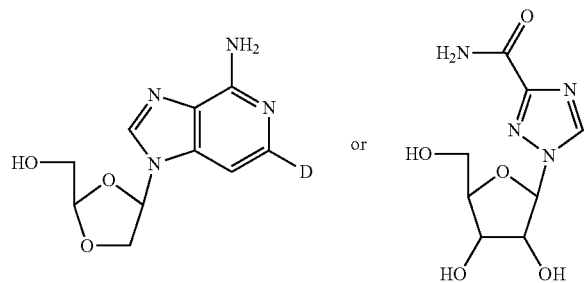

Where D is H, F, Cl or Br, preferably F or Cl, more preferably Cl,

Or pharmaceutically acceptable salts, solvates or polymorphs thereof.

In alternative embodiments, the compound as described hereinabove, may be conjugated to an antibody (monoclonal or polyclonal) which binds to MeCP2 or EZH2 (anti-MECP2 or anti-EZH2). Alternatively, the above antibodies may be used in the absence of conjugation to inhibit MeCP2 or EZH2 in order to inhibit fibrogenesis in a patient or subject, including liver fibrogenesis and to treat cirrhosis of the liver, as well as fibrotic disease and disease states and conditions which occur secondary to fibrogenesis and/or fibrotic disease.

The present invention also relates to pharmaceutical compositions comprising an effective amount of any one or more of the compounds described above (especially compounds conjugated to mono and/or polyclonal antibodies), optionally in combination with a pharmaceutically acceptable carrier, additive or excipient.

Thus, the present application is directed to the inhibition of fibrogenesis, including liver fibrogenesis in a patient in need thereof, and/or the treatment of cirrhosis of the liver (which may be caused for example, by a virus, a chemical or drug) comprising administering an effective amount of one or more compounds or anti-MeCP2 and/or anti-EZH2 antibodies (including compounds conjugated to anti-MECP2 and/or anti-EZH2 antibodies) according to the present invention optionally in combination with a pharmaceutically acceptable carrier, additive or excipient to said patient. Pharmaceutical compositions based upon these antibodies and/or nucleoside compounds in effective amounts in combination with a pharmaceutically acceptable carrier, additive or excipient are additional aspects of the present invention.

The present invention also relates to the inhibition of methylation of DNA and RNA in cells comprising exposing cells, especially including liver cells to an effective of a compound as otherwise disclosed herein. A method of inhibiting the methylation of DNA and/or RNA in cells, especially liver cells, in a patient comprises administering an effective amount of a compound as otherwise described herein to said patient.

The present invention also relates to method for inhibiting and/or treating fibrotic diseases including, for example, liver fibrosis (alcoholic, viral, autoimmune, metabolic and hereditary chronic disease), renal fibrosis (e.g., resulting from chronic inflammation, infections or type II diabetes), lung fibrosis (idiopathic or resulting from environmental insults including toxic particles, sarcoidosis, asbestosis, hypersensitivity pneumonitis, bacterial infections including tuberculosis, medicines, etc.), interstitial fibrosis, systemic scleroderma (autoimmune disease in which many organs become fibrotic), macular degeneration (fibrotic disease of the eye), pancreatic fibrosis (resulting from, for example, alcohol abuse and chronic inflammatory disease of the pancreas), fibrosis of the spleen (from sickle cell anemia, other blood disorders) cardiac fibrosis (resulting from infection, inflammation and hypertrophy), mediastinal fibrosis, myelofibrosis, endomyocardial fibrosis, retroperitoneal fibrosis, progressive massive fibrosis, nephrogenic systemic fibrosis, fibrotic complications of surgery, especially surgical implants, injection fibrosis and secondary conditions and disease states of fibrosis. Secondary conditions and disease states which occur as a consequence of or associated with fibrosis include for example, cirrhosis, diffuse parenchymal lung disease, postvasectomy pain syndrome and rheumatoid arthritis, among others. The method according to the present invention comprises administering an effective amount of one or more compounds according to the present invention to a patient at risk for a fibrotic disease or in need of therapy for a fibrotic disease or secondary disease state or condition thereof, optionally in combination with a pharmaceutically acceptable carrier, additive or excipient.

DETAILED DESCRIPTION OF THE INVENTION

Figure 1:
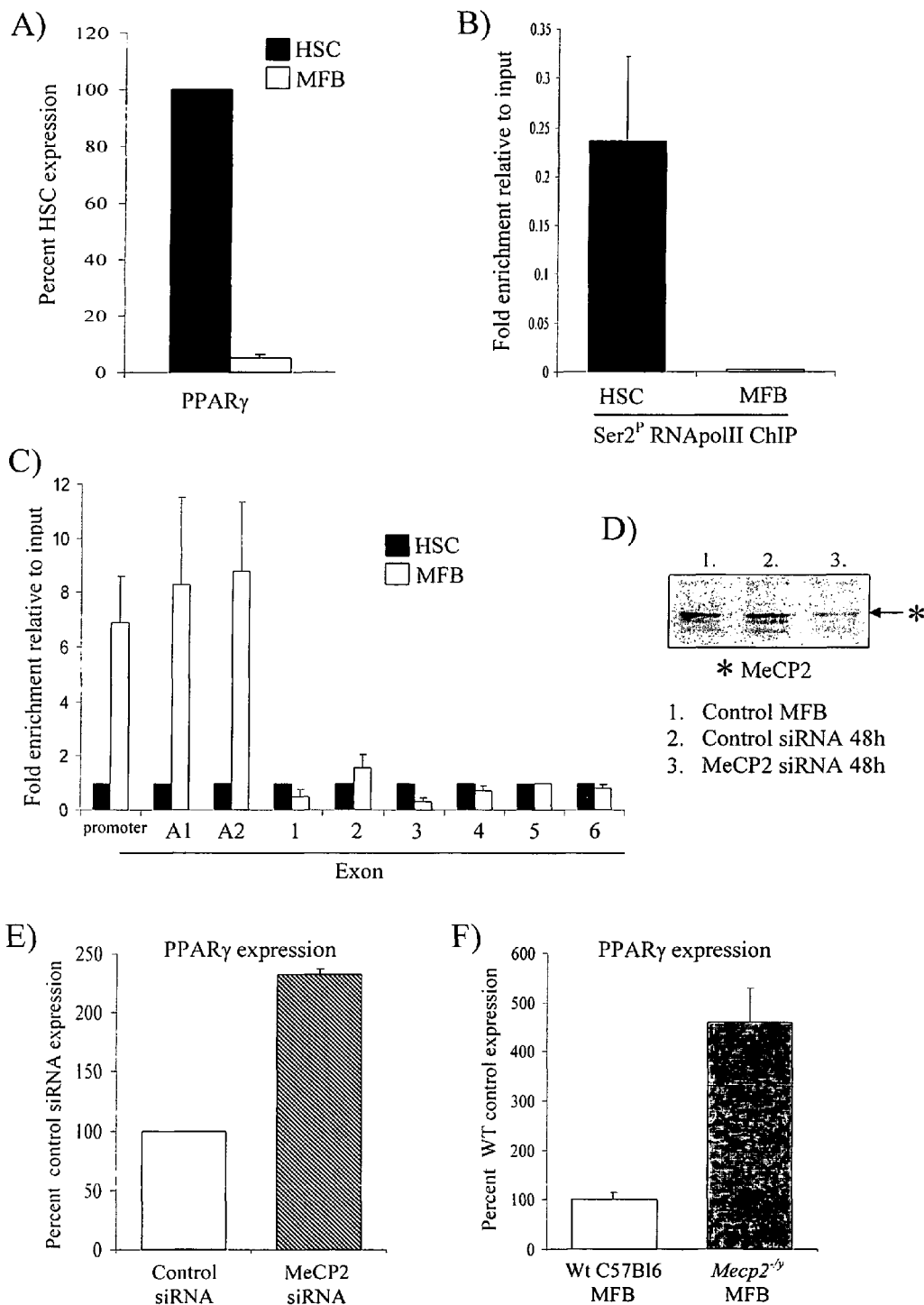
FIG. 1—A.) PPARγ expression in rat HSCs and MFB—Total RNA isolated from day 0 freshly isolated rat HSCs and day 10 cultures of same cells which had undergone MTF to become MFB. First strand cDNA was synthesised which was then utilised as a template in qPCR using primers for specific amplification of rat PPARγ. The relative level of transcriptional difference was calculated and expressed as an average±SEM from three independent cell preparations. Results are expressed as percent of PPARγ expression in HSCs. B.) 100 μg of crosslinked chromatin obtained from rat HSC or MFB was incubated with 10 μg of anti RNAPolII phospho Ser2. The protein/DNA complexes were immunoprecipitated using blocked StaphA membranes. DNA component of the immunoprecipitated complexes was separated from protein fraction using phenol/chloroform extraction followed by ethanol immunoprecipitation. Obtained DNA was used as template in qPCR reactions containing rat PPARγ exon A1 specific primers. C.) 100 μg of crosslinked chromatin obtained from rat HSC or MFB was incubated with 10 μg of anti MeCP2 antibody. The protein/DNA complexes were immunoprecipitated using blocked StaphA membranes. Following the reversal of crosslinks, DNA component of the immunoprecipitated complexes was separated from protein fraction using phenol/chloroform extraction followed by ethanol immunoprecipitation. Obtained DNA was used as template in qPCR reactions containing rat PPARγ exons A1, A2 and 1-6 specific primers. Negative control and baseline were set as 1 and remaining values shown in relation to this as fold enrichment relative to total input. D.) $5\times10^6$ rat MFBs were electroporated as outlined in "Materials and methods". 2 μgs total siRNA designed to target rat MeCP2 was used per transfection. Control siRNA used was a validated, non-targeting siRNA. Total RNA was prepared from control or rat MeCP2 siRNA transfected cells 48 h after the electroporation. First strand cDNA was synthesised which was then utilised as a template in qPCR using primers for specific amplification of rat PPARγ. E.) Quiescent HSCs were isolated from wild type C57Bl6 or mecp2$^{-/y}$ mice and allowed to transdifferentiate in vitro for 14 days. Total RNA was prepared from both C57Bl6 and mecp2$^{-/y}$ MFB cell populations and first strand cDNA synthesised which was then utilised as a template in qPCR using primers for specific amplification of mouse PPARγ. The relative level of transcriptional difference was calculated and expressed as an average±SEM from three independent cell preparations. Results are expressed as percent of PPARγ expression in wild type C57Bl6 MFBs. f.) A five-fold increased expression of PPARγ mRNA was observed in MeCP2 deficient Mecp2$^{-/y}$ mouse myofibroblasts compared with wild type (Wt) myofibroblasts.

The following terms shall be used to describe the present invention. In instances where a term is not specifically defined herein, the definition given to that term is that which is used within the context of the present invention by those of ordinary skill in the art.

"Patient" or "subject" refers to an animal, preferably a mammal, even more preferably a human, in need of treatment or therapy to which compounds according to the present invention are administered in order to inhibit fibrogenesis, including liver fibrogenesis, or treat a fibrotic disease or a condition or disease state which occurs secondary or as a consequence of fibrogenesis and is treatable using compounds according to the present invention.

The terms "fibrogenesis" and "fibrosis" are used synonymously throughout the specification to describe the process of forming or developing excess fibrous connective tissue in an organ or tissue as a reparative or reactive process, as opposed to a formation of fibrous tissue as a normal constituent of an organ or tissue. Fibrogenesis is the process of forming fibrous tissue usually by degeneration (e.g., fibrosis of the pulp) and a proliferation of fibroblasts. Fibrogenesis is an abnormal condition in which fibrous connective tissue spreads over or replaces normal smooth muscle or other normal organ tissue. Fibrogenesis is most common in the heart, lung, peritoneum, and kidney, but may occur elsewhere. In the present invention, the term "fibrosis" is used to distinguish abnormal from normal healing processes. There are a number of disease states or conditions which are caused by fibrogenesis including for example, liver (alcoholic, viral, autoimmune, metabolic and hereditary), renal (chronic imflammation, infection, type II diabetes) lung fibrosis (idiopathic or resulting from environmental insults including toxic particles, sarcoidosis, asbestosis, hypersensitivity pneumonitis, bacterial infections including tuberculosis, medicines, etc.) and pancreatic fibrosis (alcohol abuse, chronic inflammatory disease of the liver), systemic scleroderma (autoimmune disease resulting in fibrosis in numerous organs), macular degeneration, cardiac fibrosis, cystic fibrosis of the pancreas and lungs, injection fibrosis, which can occur as a complication of intramuscular injections, especially in children, endomyocardial fibrosis, systemic idiopathic fibrosis, idiopathic pulmonary fibrosis (lung), mediastinal fibrosis, myelofibrosis, retroperitoneal fibrosis, progressive massive fibrosis (which is a complication of coal worker's pneumoconiosis), nephrogenic systemic fibrosis, nodular subepidermal fibrosis (e.g, benign fibrous histiocytoma, pleural fibrosis, fibrosis as a consequence of surgery (e.g., surgical implants), proliferative fibrosis, pipestem fibrosis, postfibrinous fibrosis, bridging fibrosis, and radiation fibrosis, among others.

Disease states or conditions which are found or occur secondary to fibrosis include for example, cirrhosis, diffuse parenchymal lung disease, post-vasectomy pain syndrome and rheumatoid arthritis, among others.

The term "compound" is used herein to refer to any specific chemical compound disclosed herein, including compounds which are conjugated to mono and/or polyclonal antibodies to MeCP$_2$ and/or EZH$_2$. Within its use in context, the term generally refers to a single compound, but in certain instances may also refer to stereoisomers and other positional isomers and/or optical isomers (including racemic mixtures) of disclosed compounds. The compounds of this invention include all stereoisomers where relevant (e.g., cis and trans isomers, such as of vinyl groups) and all optical isomers of the present compounds (eg., R and S enantiomers), as well as racemic, diastereomeric and other mixtures of such isomers, as well as all polymorphs and hydrates of the present compounds, where applicable. Note that a dashed line -------- which represents a bond between two atoms in a compound signifies that the bond may be a single bond or a double bond in context, depending upon the substituents (if any) on the atoms to which the dashed line is attached. By way of example, in exemplary purine compounds according to the invention, where G is an oxygen atom (O), the bond between O and the carbon atom to which it is attached is a double bond and the bond between the carbon to which the oxygen is bonded and the alpha nitrogen is a single bond, and E (which is bonded to the nitrogen atom alpha to the carbon) is H. When G is a $NR^{1a}R^2$ group, then the bond between $NR^{1a}R^2$ and the carbon atom to which it is attached is a single bond and the bond between the carbon to which the nitrogen of $NR^{1a}R^2$ is bonded and the alpha nitrogen is a double bond, and E (which is bonded to the nitrogen atom alpha to the carbon) is non-existent.

"Hydrocarbon" or "hydrocarbyl" refers to any monovalent radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups, including aromatic groups both substituted and unsubstituted.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_{20}$ alkyl groups, more preferably $C_1$-$C_6$ alkyl groups. "Alkylene" refers to a fully saturated hydrocarbon which is divalent (may be linear, branched or cyclic) and which is optionally substituted. The term "ether" shall mean a $C_1$ to $C_{20}$ ether group, formed from an oxygen and an alkyl group at a position on the sugar moiety of compounds according to the present invention, or alternatively, may also contain at least one oxygen group within the alkyl chain.

The term "acyl" is used throughout the specification to describe a group on a free amine or hydroxyl position (e.g., in the carbocyclic moiety or the nucleoside base) which contains a $C_1$ to $C_{20}$ linear, branched or cyclic alkyl chain. The acyl group at the 5' position, in combination with the 5' hydroxyl group results in an ester, which, after administration, may be cleaved to produce the free nucleoside form of the present invention. Acyl groups according to the present invention are represented by the structure:

where $R^4$ is a $C_1$ to $C_{20}$ linear, branched or cyclic alkyl group, alkoxyalkyl (including an ethylene oxide chain which may end in a free hydroxyl group or a $C_1$-$C_{10}$ alkyl group and ranges in molecular weight from about 50 to about 40,000 or about 200 to about 5,000), such as phenoxymethyl, aryl, alkoxy, alkoxycarbonyloxy groups (e.g., [(isopropoxycarbonyl)oxy]-methoxy), aryloxyalkyl, among others, all of which groups may be optionally substituted. Preferred acyl groups are those where $R^4$ is a $C_1$ to $C_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others and may include such related groups as sulfone groups such as mesylate groups. All groups may be appropriately substituted within context as otherwise described herein. One of ordinary skill in the art will recognize the acyl groups which will have utility in the present invention, either to synthesize the target pharmaceutical compounds or as prodrug of the nucleosides according to the present invention.

The term "amino acid" or "amino acid residue" shall mean, within context, a radical of a D- or L-amino acid which is covalently bound to a nucleoside analog at the 4' exocyclic amine position of the cytosine base or the 5'- or 3'-OH position of the sugar synthon ($R^2$, $R^1$ or $R^{1a}$) through a carboxylic acid moiety of the amino acid, thus forming respectively, an amide or ester group linking the nucleoside to the amino acid. Representative amino acids include both natural and unnatural amino acids, preferably including, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others.

The term "phosphate ester" or "phosphodiester" is used throughout the specification to describe mono-phosphate groups at the 5' position of the carboyclic sugar synthon which are mono- or diesterified such that the phosphate group is negatively charged or is rendered neutral, i.e., has a neutral charge. Phosphate esters for use in the present invention include those represented by the structures:

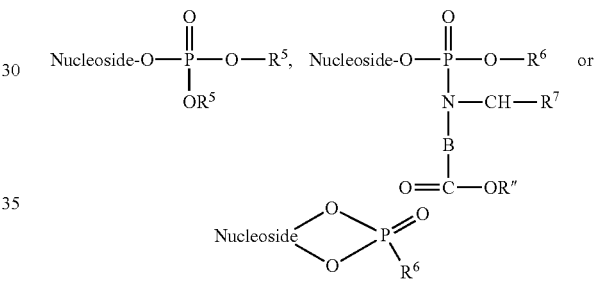

where each $R^5$, $R^6$ and R" is independently selected from H, a $C_1$ to $C_{20}$ linear, branched or cyclic alkyl group, alkoxyalkyl, aryloxyalkyl, such as phenoxymethyl, aryl and alkoxy, among others, including alkoxycarbonyloxy groups (e.g., (isopropoxycarbonyl)oxy]-methoxy) with the proviso that at least one $R^5$ group is other than H, or the two $R^5$ groups together form a five- or six-membered heterocyclic group, B is a direct bond (N directly bonded to C of the ester/carboxylic acid group) or a $C_1$-$C_3$ alkylene group optionally substituted with a $C_1$-$C_3$ alkyl group, preferably a methyl group and $R^7$ is a $C_1$ to $C_{20}$ linear, branched or cyclic alkyl or acyl group, alkoxyalkyl, aryloxyalkyl, such as phenoxymethyl, aryl and alkoxy, among others, each of which groups previously mentioned may be optionally substituted. Preferred monophosphate esters for use in prodrug forms according to the present invention are those where $R^5$ is a $C_1$ to $C_{20}$ linear or branched chain alkyl group, more preferably a $C_1$ to $C_3$ alkyl group, all of which groups may be optionally substituted.

Other terms used to indicate substituent groups in compounds according to the present invention are as conventionally used in the art.

"Aryl" or "aromatic" refers to a substituted or unsubstituted monovalent aromatic radical having a single ring (e.g., benzene) or multiple condensed rings (e.g., naphthyl, anthracenyl, phenanthryl), which may be optionally substituted and can be can be bound to the compound according to the present invention at any position on the ring(s) (preferably, for example, benzyl).

The term "cyclic" shall refer to an optionally substituted carbocyclic or heterocyclic group, preferably a 3-7-membered ring, preferably a 5- or 6-membered ring. A heterocyclic ring or group shall be a ring containing between 3 and 7 atoms of which up to four of those atoms are other than carbon and are selected from nitrogen, sulfur and oxygen. Carbocyclic and heterocyclic rings according to the present invention may be unsaturated or saturated.

The term "effective" or "effective amount" refers to the amount of a selected compound which is effective within the context of its use or administration. In the case of therapeutic methods according to the present invention, the precise amount required will vary depending upon the particular compound selected, the age and weight of the subject, route of administration, and so forth, but may be easily determined by routine experimentation. Compounds according to the present invention may be used to treat, inhibit or reduce the likelihood of fibrosis, fibrotic disease and/or conditions or disease states which occur secondary to fibrosis, as well as reducing the likelihood of viral infections (by for example, inhibition the growth, replication or elaboration of the virus).

The term "substituted" shall mean substituted at a carbon (or nitrogen) position with, in context, hydroxyl, carboxyl, cyano (C≡N), nitro (NO$_2$), halogen (preferably, 1, 2 or 3 halogens, especially on an alkyl, especially a methyl group such as a trifluoromethyl), thiol, alkyl group (preferably, $C_1$-$C_6$, more preferably, $C_1$-$C_3$), alkoxy group (preferably, $C_1$-$C_6$ alkyl or aryl, including phenyl), ester (preferably, $C_1$-$C_5$ alkyl or aryl) including alkylene ester (such that attachment is on the alkylene group, rather than at the ester function which is preferably substituted with a $C_1$-$C_6$ alkyl or aryl group), thioether (preferably, $C_1$-$C_6$ alkyl or aryl), thioester (preferably, $C_1$-$C_5$ alkyl or aryl), (preferably, $C_1$-$C_6$ alkyl or aryl), halogen (F, Cl, Br, I), nitro or amine (including a five- or six-membered cyclic alkylene amine, including a $C_1$-$C_6$ alkyl amine or $C_1$-$C_6$ dialkyl amine), alkanol (preferably, $C_1$-$C_6$ alkyl or aryl), or alkanoic acid (preferably, $C_1$-$C_6$ alkyl or aryl). Preferably, the term "substituted" shall mean within its context of use alkyl, alkoxy, halogen, hydroxyl, carboxylic acid, nitro and amine (including mono- or di-alkyl substituted amines). The term unsubstituted shall mean substituted with one or more H atoms.

The term "virus" shall be used to describe all types of viruses which produce fibrogenesis, including liver fibrogenesis and/or cause or exacerbate cirrhosis of the liver, as well as other disease states or conditions which occur secondary to fibrogenesis.

The term "enantiomerically enriched" or "ee" is used throughout the specification to describe a nucleoside which includes at least about 95%, preferably at least about 96%, more preferably at least about 97%, even more preferably, at least about 98%, and even more preferably at least about 100% or more of a single enantiomer of that nucleoside. Compounds according to the present invention are generally β-D-nucleoside compounds. When the present compounds according to the present invention are referred to in this specification, it is presumed that the nucleosides have the D-nucleoside configuration and are enantiomerically enriched (preferably, about 100% of the D-nucleoside), unless otherwise stated.

The terms "coadminister" and "coadministration" are used synonymously to describe the administration of at least one of the nucleoside compounds and/or antibodies according to the present invention in combination with at least one other agent. While it is preferred that coadministered agents be administered at the same time, agents may be administered at times such that effective concentrations of both (or more) agents appear in the patient at the same time for at least a brief period of time.

The term "independently" is used herein to indicate that the variable, which is independently applied, varies independently from application to application.

Compounds according to the present invention may be used in pharmaceutical compositions having biological/pharmacological activity for the treatment, inhibition or reducing the likelihood of fibrogenesis, including liver fibrogenesis and other forms of fibrogenesis or fibrotic disease, as well as a number of other conditions and/or disease states which may appear or occur secondary to fibrogenesis, as otherwise described herein. These compositions comprise an effective amount of any one or more of the compounds disclosed hereinabove, optionally in combination with a pharmaceutically acceptable additive, carrier or excipient. In addition, compounds according to the present invention may be used to inhibit methylation of polynucleotides, in particular, DNA and RNA in numerous tissue and cells in a patient, including liver cells. While not be limited by way of theory, it is believed that this mechanism is responsible, at least in part, for the activity shown by compounds in inhibiting fibrogenesis, including liver fibrogenesis and/or in treating cirrhosis of the liver, as well as numerous other fibrotic diseases and/or disease states or conditions which occur secondary to fibrogenesis. Compounds according to the present invention may also be used as intermediates in the synthesis of compounds exhibiting biological activity as well as standards for determining the biological activity of the present compounds as well as other biologically active compounds.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously. Administration will also be depend upon the tissue in which fibrogenesis and/or related disease states or conditions occur.

Sterile injectable forms of the compositions of this invention may be aqueous or oleaginous suspension, especially when an antibody is used alone or conjugated to a nucleoside compound disclosed herein. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol.

Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye (especially macular degeneration), the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of novel nucleoside of the instant invention that may be combined with the carrier materials to produce a single dosage form will vary depending upon the host treated, the particular mode of administration. Preferably, the compositions should be formulated so that a dosage of at least about 0.005 mg/kg, between about 0.01 and 150 mg/kg, preferably about 0.5 to about 25 mg/kg of patient/day of the nucleoside according to the present invention can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to inhibit fibrogenesis (fibrosis) as otherwise described herein, especially liver fibrogenesis, or to treat, prevent or delay the onset of cirrhosis. Preferably, to treat, prevent or delay the onset of cirrhosis, the compositions will be administered in oral dosage form in amounts ranging from about 250 micrograms up to about 500 mg or more at least once a day, preferably, up to four times a day, within the dosage range used for therapeutic treatment. The present compounds are preferably administered orally, but may be administered parenterally, topically, in suppository or other form.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other agents for the treatment of liver fibrogenesis and/or cirrhosis of the liver in an individual to be treated. Certain compounds according to the present invention may be effective for enhancing the biological activity of certain agents according to the present invention by reducing the metabolism or inactivation of other compounds and as such, are co-administered for this intended effect.

The present invention is now described, purely by way of illustration, in the following further description and the attached examples. It will be understood by one of ordinary skill in the art that these examples are in no way limiting and that variations of detail can be made without departing from the spirit and scope of the present invention.

The hepatic stellate cell occupies the space between hepatocytes on one side and endothelial cells and the hepatic sinusoid on the other side. This location enables the hepatic stellate cell to be a sensor for hepatocyte and endothelial cell damage, inflammation and microbial products from the bloodstream (Frideman S L, 2008). Hepatic stellate cells therefore provide a mechanism for activation of a rapid innate wound-healing response to environmental insults. The vast number of changes in gene expression that underpin MTD suggests an extensive reprogramming of the cellular epigenome is required in order to suppress the adipogenic features of the quiescent hepatic stellate cell in favour of the acquisition of the myofibroblast phenotype (De Minicis S et al 2007, She H et al 2005, Tsukamoto H et al 2006). It is critical that this epigenome reprogramming is under tight regulation since inappropriate MTD would lead to the formation of unwanted scar tissue and promote the development of fibrosis (Friedman S L, 2008). The regulatory mechanisms that orchestrate the changes in gene expression during MTD remain poorly defined.

PPARγ expression is associated with the adipogenic features of the quiescent hepatic stellate cell and must be silenced for the cell to adopt its myofibroblastic characteristics including entry to the cell cycle and expression of the major protein constituent of scar tissue, type I collagen (She H et al 2005, Tsukamoto H et al 2006). Forced over-expression of PPARγ in hepatic myofibroblasts results in reversion of MTD with down-regulation of type I collagen, loss of proliferation and reacquisition of their adipogenic characteristics. Given the pivotal regulatory role played by PPARγ in MTD, we reasoned that investigation of its transcriptional regulation in hepatic stellate cells would lead to the discovery of novel and critical regulators of MTD and wound-healing.

Figure 2:
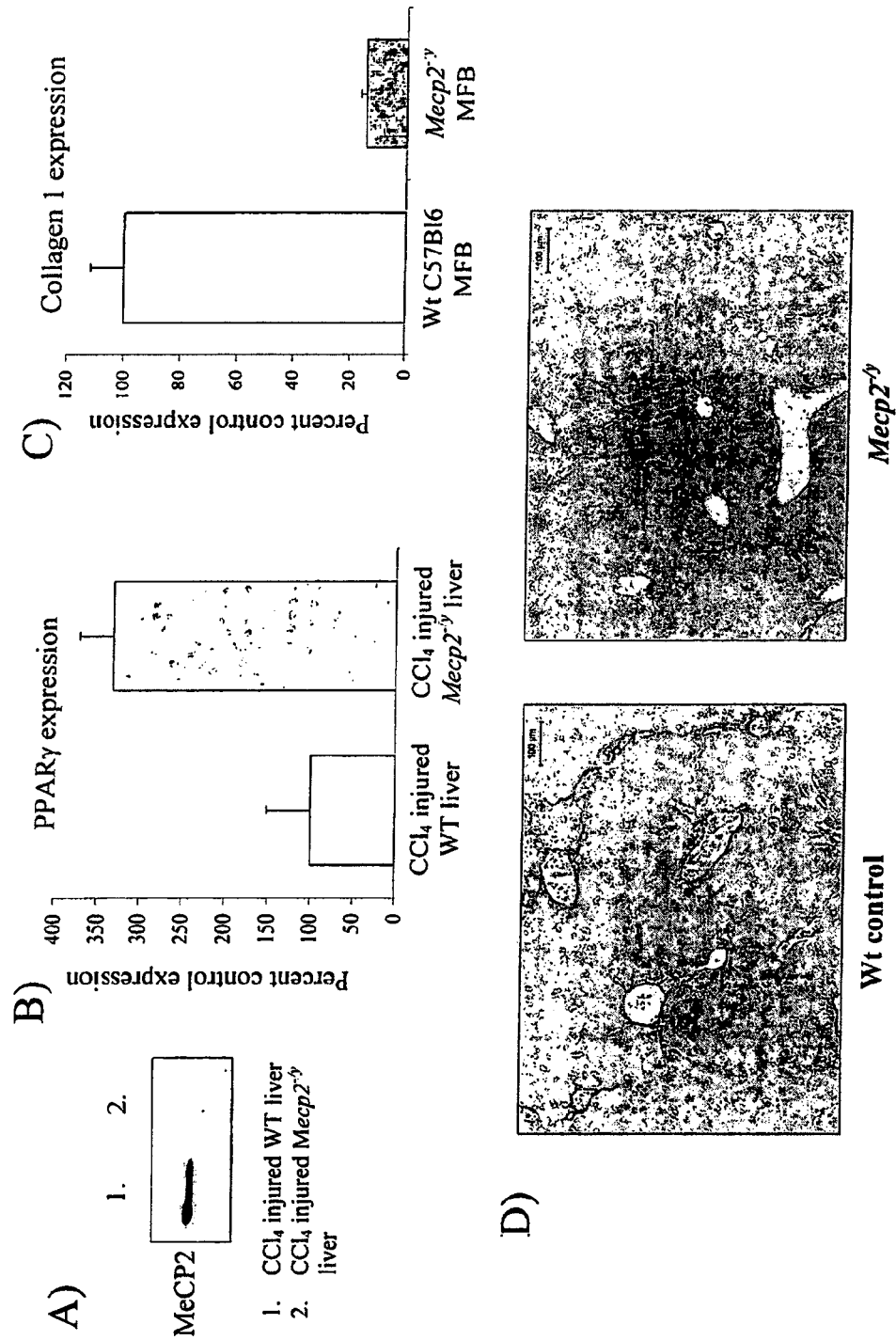
FIG. 2—A.) A small piece of frozen $CCl_4$ injured wild type or mecp2$^{-/y}$ liver was mashed up and resuspended in PBS. Protein concentration of cell suspension was determined and 200 μg whole cell extract denatured in SDS loading buffer and proteins separated by SDS PAGE. Protein was transferred onto membrane and immunoblotted for MeCP2. Representative of two separate experiments is shown. B.) RNA was isolated from a small piece of frozen $CCl_4$ injured wild type or mecp2$^{-/y}$ liver. First strand cDNA was synthesised which was then utilised as a template in qPCR using primers for specific amplification of mouse PPARγ. Results are expressed as percent of PPARγ expression in wild type $CCl_4$ injured liver. C.) Quiescent HSCs were isolated from wild type C57Bl6 or mecp2$^{-/y}$ mice and allowed to transdifferentiate in vitro for 14 days. Total RNA was prepared from both C57Bl6 and mecp2$^{-/y}$ MFB cell populations and first strand cDNA synthesised which was then utilised as a template in qPCR using primers for specific amplification of mouse collagen 1. The relative level of transcriptional difference was calculated and expressed as an average±SEM from three independent cell preparations. Results are expressed as percent of collagen 1 expression in wild type C57Bl6 MFBs. D.) Sirius Red immunostaining on sections cut from a chronically (3 weeks) $CCl_4$ injured wild type C57Bl6 or mecp2$^{-/y}$ livers. Photomicrographs taken at ×5 magnification show greater collagen deposition in wild type as compared to mecp2$^{-/y}$ hemizygote animals indicative of a more severe fibrosis grade.
Figure 6:
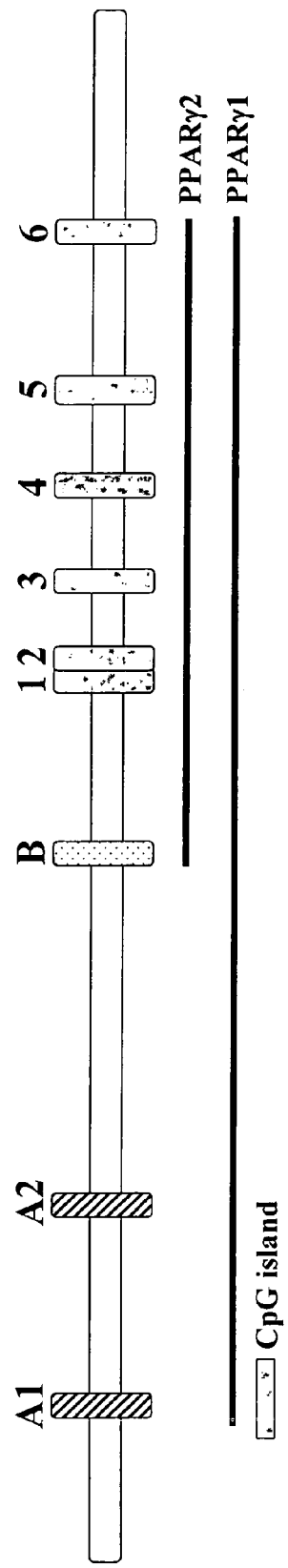
FIGS. 6 and 7 shows exons A1 and A2 of the PPARγ gene which are spanned by a methylated CpG island.
Figure 7:
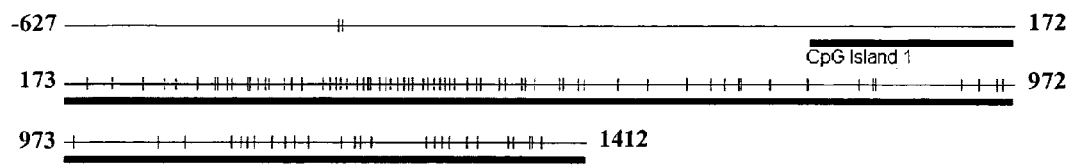
Figure 8:
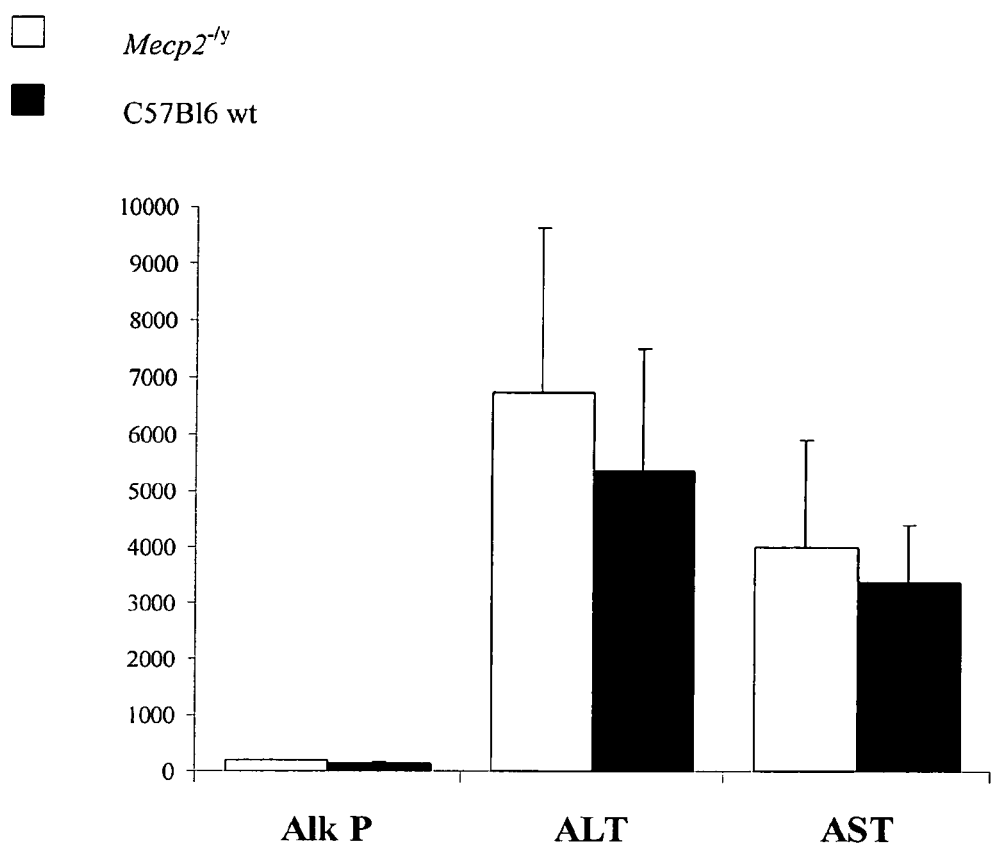
FIG. 8. To rule out a possibility that MeCP2 hemizygosity was simply attenuating hepatocellular damage caused by CCl4, plasma ALT levels were measured as a standard parameter of liver injury. As the ALT levels were similar between Wt and Mecp2$^{-/y}$ mice and hepatic MeCP2 expression is selective for myofbroblasts, the inventors conclude that deletion of MeCP2 protects against fibrosis due to the loss of its influence on MTD and wound-healing.

The in vitro culture of freshly isolated primary hepatic stellate cells provides a widely accepted model that recapitulates the majority of phenotypic changes observed for MTD in the injured liver (Friedman S L 2008, De Minicis S et al 2007). In this model, freshly isolated hepatic stellate cells are cultured on plastic in serum-containing media and over a period of roughly 7 days undergo a step-wise transformation into a myofibroblastic phenotype. Culture-induced MTD of hepatic stellate cells is associated with a greater than 95% loss of PPARγ transcript (FIG. 1A) and as determined by cross-linked ChIP, depletion of elongating RNA polymerase II (P-Ser$^2$-RNAP) at the PPARγ gene (FIG. 1B). This coincided with recruitment of the methyl-CpG binding protein MeCP2 to the promoter and exons A1 and A2 of the PPARγ gene (FIG. 1C) which are spanned by a methylated CpG island (FIGS. 6 and 7). Since MeCP2 is a powerful epigenetic repressor of gene transcription we investigated the possibility that it controls silencing of PPARγ expression during MTD (Chadwick and Wade 2007). siRNA knockdown of MeCP2 in myofibroblasts (FIG. 1D) resulted in elevated PPARγ transcript expression (FIG. 1E), furthermore a 5-fold increased expression of PPARγ mRNA was observed in MeCP2 deficient Mecp2$^{-/y}$ mouse myofibroblasts compared with wild type (Wt) myofibroblasts (FIG. 1F). MeCP2 expression is barely detectable in the normal liver but is induced selectively in myofibroblasts of the injured liver (Mann et al, 2007). To investigate a wound-healing role for MeCP2 in vivo we compared hepatic PPARγ expression between Wt and Mecp2$^{-/y}$ mice that had been repeatedly injured with the hepatotoxin carbon tetrachloride (CCl$_4$) which causes chronic hepatic wound-healing/fibrogenesis (Iredale JP JCI-2007). Absence of hepatic MeCP2 (FIG. 2A) resulted in higher PPARγ mRNA expression in the injured liver (FIG. 2B). PPARγ is a negative regulator of the expression of type I collagen, the major fibrogenic collagen produced by myofibroblasts in response to injury (Yavrom et al, 2005). Expression of hepatic type I collagen was reduced by 90% in injured Mecp2$^{-/y}$ mice compared to Wt (FIG. 2C). Sirius red staining of injured Wt livers detected tracts of fibrotic collagen-rich matrix that formed bridges between hepatic vessels (FIG. 2D, left). In contrast, bridging fibrosis was not evident in injured Mecp2$^{-/y}$ livers, although thin tracts of fibrotic matrix were visible around vessels and within the spaces between hepatic parenchyma (FIG. 2D right). Blinded histopathology grading for fibrosis (on the Metavir scale of 0 for normal to 4 for cirrhosis) confirmed reduced wound-healing/fibrogenesis in Mecp2$^{-/y}$ livers with a score of grade 1 (mild fibrosis) compared with grade 3 (severe bridging fibrosis) for wild type. To rule out a possibility that MeCP2 hemizygosity was simply attenuating hepatocellular damage caused by CCl4, we measured plasma ALT levels as a standard parameter of liver injury. As the ALT levels were similar between Wt and Mecp2$^{-/y}$ mice (FIG. 8) and hepatic MeCP2 expression is selective for myofibroblasts, we conclude that deletion of MeCP2 protects against fibrosis due to the loss of its influence on MTD and wound-healing. Forced over-expression of PPARγ in hepatic myofibroblasts protects against development of fibrosis (Hazra S et al 2004, Tsukamoto H et al 2006). The attenuated fibrogenic response of the Mecp2$^{-/y}$ mouse is therefore explained, at least in part, by maintenance of PPARγ expression. However, we have previously reported that MeCP2 is also required for repression of IκBα expression during MTD of hepatic stellate cells, this being critical for the expression of NF-κB-dependent genes in the myofibroblast (Mann J et al, 2007). MeCP2 is therefore likely to operate during MTD as a coordinator of the transcriptional silencing of multiple genes associated with the quiescent phenotype of the hepatic stellate cell.

Figure 3:
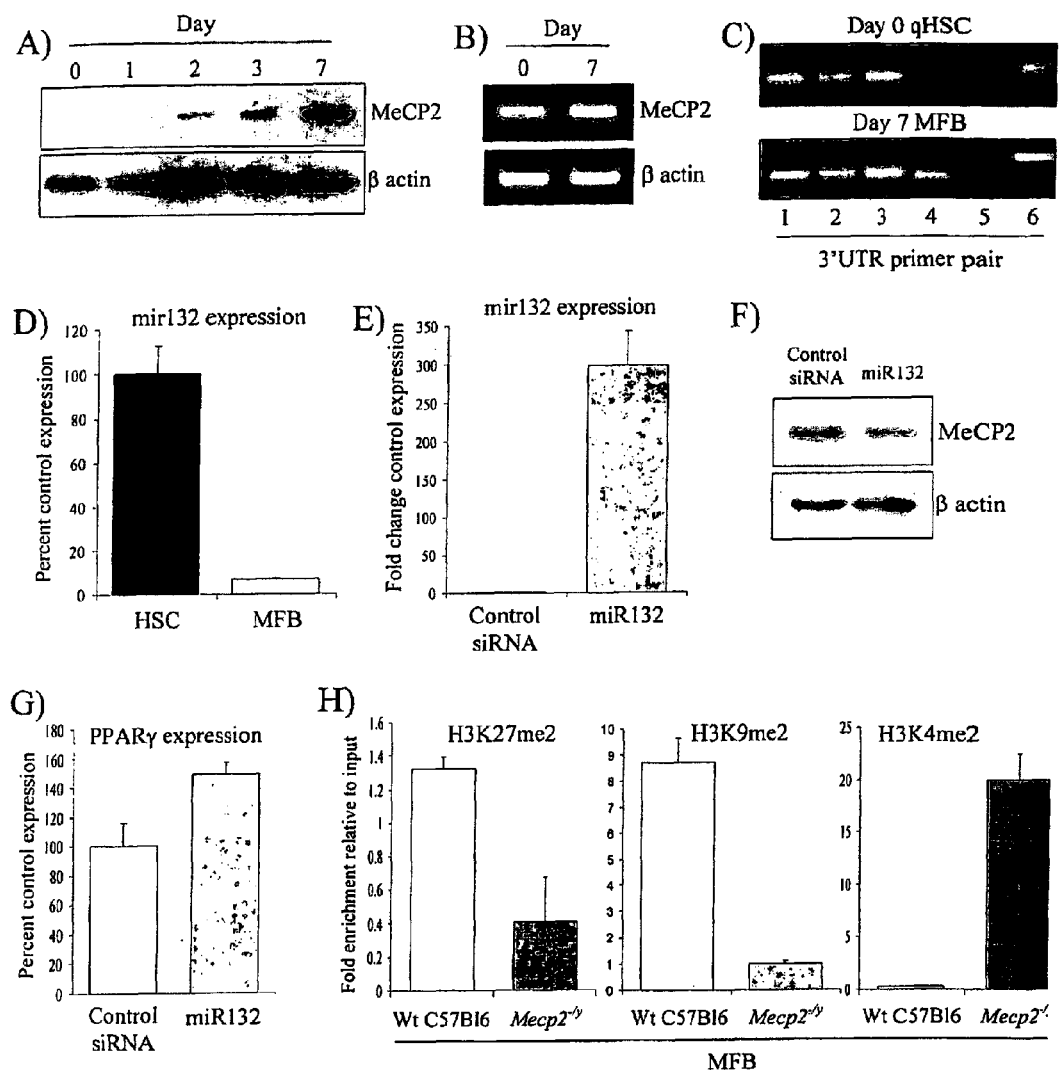
FIG. 3—A.) Freshly isolated HSCs (day 0) or HSCs/MFBs harvested at day 1, 2, 3 and 7 following the isolation were resuspended in PBS, protein concentration determined and 30 μg whole cell extract from each sample separated on SDS PAGE. Transferred protein was used to immunoblot for MeCP2 and β actin. B.) 20 ng of cDNA from quiescent HSC or MFBs was used as a template for RT-PCR with primer pair specific for MeCP2 and β actin. The PCR was carried out over 30 or 23 cycles for MeCP2 and β actin respectively. C.) 20 ng of cDNA from quiescent HSC or MFBs was used as a template for RT-PCR with primer pairs specific for sections of 3' UTR in MeCP2 mRNA. The transcripts were amplified over 30 cycles. The PCR product generated by primer pair 3'UTR1 started at 989 bp 3' of MeCP2 stop codon; 3'UTR2PCR product started at 1978 bp 3' of the stop codon; 3'UTR3 at 4063 bp at 3' of the stop codon; 3'UTR4 at 5162 bp at 3' of the stop codon; 3'UTR5 at 6868 bp at 3' of the stop codon and 3'UTR6 at 8401 bp at 3' of the stop codon. D.) Micro RNAs were isolated from quiescent HSCs and MFBs using miRNeasy mini kit. Obtained total RNA was reverse transcribed using miScript Reverse Transcription Kit and rat miR132 in the samples detected with miScript primer assay 218300. Results are expressed as percent of miR132 expression in HSCs. E.) to G.) $5\times10^6$ MFBs were mixed with 2 μg miR132 mimic or control siRNA and electroporated as outlined in "Materials and methods". Cells were harvested 48 hours later for RNA and whole cell extract preparation. Micro RNA was isolated and detected as described in D.) see FIG. 3E.) for results that are expressed as percent of miR132 expression in control siRNA transfected MFBs. F.) Whole cell extracts obtained from miR132 or control siRNA transfected MFBs were separated by SDS-PAGE and transferred protein blotted for MeCP2 and β actin. G.) cDNA obtained in E.) was further used as template in qPCR using primer pair specific for PPARγ. H.) Native chromatin was prepared from in vitro transdifferentiated C57Bl6 or mecp2$^{-/y}$ MFBs. 100 μg of native chromatin from either wild type or mecp2$^{-/y}$ MFBs was incubated with 10 μg of anti dimethyl H3K27, dimethyl H3K9 or dimethyl H3K4 and protein/DNA complexes were immunoprecipitated using blocked StaphA membranes. DNA component of the immunoprecipitated complexes was separated from protein fraction using phenol/chloroform extraction followed by ethanol immunoprecipitation. Obtained DNA was used as template in PCR reactions containing mouse PPARγ promoter specific primers. All results are expressed as values above background calculated as fold enrichment relative to total input.

As MeCP2 is important for MTD and wound-healing we were next interested to determine how its expression is controlled in hepatic stellate cells. MeCP2 protein is undetectable in hepatic stellate cells but is strongly induced with MTD (Mann J et al, 2007). Here we show that MeCP2 protein expression is induced during the early transitionary phase (day 1) of culture-induced MTD and increases in expression with each subsequent day of culture, reaching high levels when the cells have fully transdifferentiated to the myofibroblastic state (day 7). This early induction of MeCP2 supports a regulatory role for MeCP2 in transdifferentiation (FIG. 3A). However, MeCP2 transcript was detected prior to MTD indicating post-transcriptional regulation (FIG. 3B). The Mecp2 gene contains multiple polyadenylation sites and generates several transcripts which differ in their length of 3' UTR, ranging from 1.8 kb to 10 kb (Klein et al 1007). The 10 kb transcript predominates in the brain and unlike the shorter transcripts harbours recognition elements for several miRNAs including miR132 which is also enriched in the brain. As hepatic stellate cells express various neuronal characteristics (e.g. expression of synaptophysin, serotonin receptors and N-cadherin) we reasoned that they may also express the 10 kb transcript of Mecp2 and miR132. Primers located between 1 and 8.5 kb from the translational stop codon of the MeCP2 transcript were employed for RT-PCR detection of short versus long transcript. This analysis showed that hepatic stellate cells express the elongated form of MeCP2 transcript inclusive of the miR132 binding site (FIG. 3C). MTD is accompanied by a greater than 90% diminution of miR132 suggesting a dramatic reduction in miR132 activities in myofibroblasts compared with quiescent hepatic stellate cells (FIG. 3D). Transfection of miR132 increased expression of the micro RNA in myofibroblasts by 300 fold (FIG. 3E) which was associated with diminished expression of MeCP2 protein (FIG. 3F). This treatment was also accompanied by increased PPARγ mRNA expression (FIG. 3G). We conclude that MeCP2, and in turn MTD, are under the negative regulation of miR132 in quiescent hepatic stellate cells. Klein et al reported that during neuronal differentiation miR132 is induced via a CREB-dependent pathway involving CREB phosphorylation (Klein M E et al 2007). Of note, induction of CREB phosphorylation has previously been described to suppress fibrogenic characteristics of hepatic stellate cell-derived myofibroblasts (Houglum K et al, 1997). It therefore seems likely that CREB phosphorylation suppresses MTD via induction of miR132.

The inventors were next interested to determine the downstream regulatory events through which MeCP2 controls PPARγ transcription. High resolution quantitative native ChIP was employed to detect MeCP2-dependent histone methylation signatures at the PPARγ locus (FIG. 3H). Repressive signatures H3K9me2 and H3K27me2 where enriched at the gene in wild type myofibroblasts, however both of these modifications were depleted in Mecp2$^{-/y}$ myofibroblasts. By contrast the transcriptional active signature H3K4me2 was almost absent in wild type myofibroblasts but was highly enriched in Mecp2$^{-/y}$ cells. MeCP2 must therefore orchestrate multiple epigenetic events at the PPARγ chromatin. It has been previously reported that MeCP2 facilitates H3K9 methylation and that this repressive mark recruits the transcriptional repressor HP1α (Fuks et al, 2003). ChIP analysis confirmed that HP1α is recruited selectively to the promoter and exons A1 and A2 of the PPARγ gene (FIG. 4A) which coincides with the binding pattern for MeCP2 shown in FIG. 1C. Since HP1α is selectively recruited to the 5' region of the PPARγ gene in myofibroblasts and is absent from the gene in quiescent hepatic stellate cells, we conclude that MeCP2-dependent methylation of H3K9 recruits HP1α. Although HP1α is predominantly associated with heterochromatic DNA it is also found at euchromatic sites in association with transcriptionally repressed genes where it promotes a repressive chromatin structure (Cheutin T et al 2003). Hence one mechanism by which MeCP2 regulates transcriptional silencing of PPARγ during MTD of hepatic stellate cells is the recruitment of HP1α to methylated H3K9 at the 5' region of the PPARγ gene.

Figure 4:
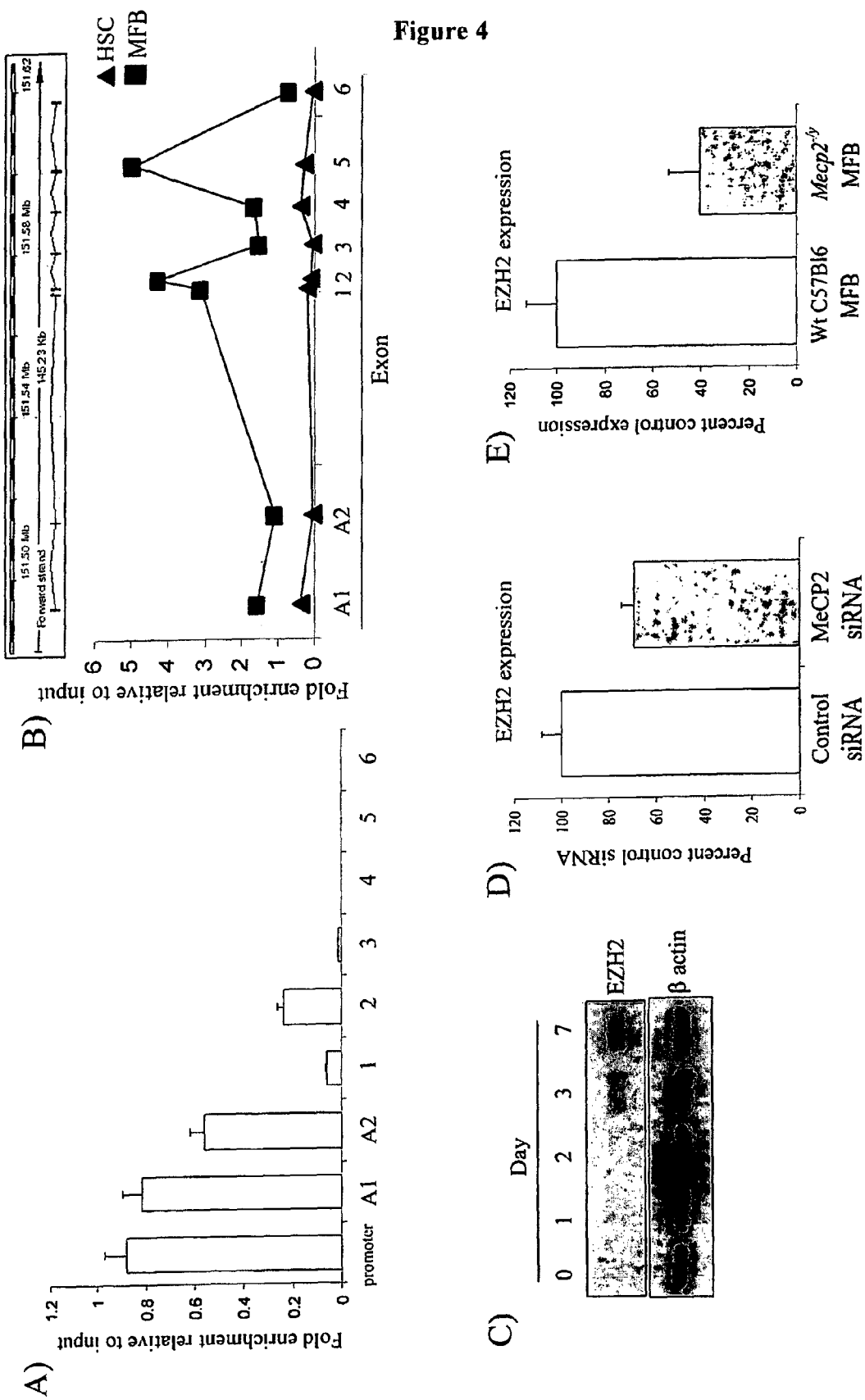
FIG. 4—A.) 100 μg of crosslinked chromatin obtained from rat MFB was incubated with 10 μg of anti HP1α. The protein/DNA complexes were immunoprecipitated using blocked StaphA membranes. Following the reversal of crosslinks, DNA component of the immunoprecipitated complexes was separated from protein fraction using phenol/chloroform extraction followed by ethanol immunoprecipitation. Obtained DNA was used as template in qPCR reactions containing rat PPARγ exons A1, A2 and 1-6 specific primers. All results are expressed as values above background calculated as fold enrichment relative to total input. B.) 100 μg of native chromatin prepared from rat HSCs or MFBs was incubated with 10 μg of anti dimethyl H3K27 antibody. The protein/DNA complexes were immunoprecipitated using blocked StaphA membranes. DNA component of the immunoprecipitated complexes was separated from protein fraction using phenol/chloroform extraction followed by ethanol immunoprecipitation. Obtained DNA was used as template in PCR reactions containing rat PPARγ promoter and exons A1, A2 and 1-6 specific primers. All results are expressed as values above background calculated as fold enrichment relative to total input. C.) Freshly isolated HSCs (day 0) or HSCs/MFBs harvested at day 1, 2, 3 and 7 following the isolation were resuspended in PBS, protein concentration determined and 30 μg whole cell extract from each sample separated on SDS PAGE. Transferred protein was used to immunoblot for EZH2 and β actin. D.) $5\times10^6$ rat MFBs were electroporated as outlined in "Materials and methods". 2 μgs total control siRNA or siRNA designed to target rat MeCP2 was used per transfection. Total RNA was prepared from control or rat MeCP2 siRNA transfected cells 48 h after the electroporation. First strand cDNA was synthesised which was then utilised as a template in qPCR using primers for specific amplification of EZH2. E.) Quiescent HSCs were isolated from wild type C57Bl6 or mecp2$^{-/y}$ livers and allowed to transdifferentiate in vitro for 14 days. Total RNA was prepared from C57Bl6 and mecp2$^{-/y}$ MFB cell populations and first strand cDNA synthesised which was then utilised as a template in qPCR analysis of EZH2 expression. The relative level of transcriptional difference was calculated and expressed as an average±SEM from three independent cell preparations. Results are expressed as percent of EZH2 expression in wild type C57Bl6 MFBs.

The observation that methylation of H3K27 was depleted in Mecp2$^{-/y}$ myofibroblasts was of interest as to date there is no known association between MeCP2 and this histone modification. ChIP analysis showed that H3K27 methylation (H3K27me2) is barely detected at the PPARγ gene in quiescent hepatic stellate cells but is enriched at exons 1 to 5 in myofibroblasts (FIG. 4B). As exons 1 to 5 are downstream of the sites at which MeCP2 is recruited (FIG. 1C), MeCP2 is unlikely to be directly responsible for H3K27 methylation but may instead regulates this modification through an indirect mechanism. Methylation of H3K27 is specifically mediated by the evolutionary conserved polycomb repressor complex 2 (PRC2) and in particular by its constituent H3K27 methyltransferase EZH2 (Kirmizis et al, 2004, Schotta et al, 2004). EZH2 protein expression is absent in quiescent hepatic stellate cells and is induced with MTD, but later (day 3 of culture) than observed for MeCP2 (FIG. 4C). Cells depleted of MeCP2 by siRNA treatment expressed lower levels of EZH2 compared with control cultures (FIG. 4D). We also measured 60% lower EZH2 transcript expression in Mecp2$^{-/y}$ myofibroblasts compared with wild type cells. These results reveal an unexpected role for MeCP2 as a positive regulator of EZH2 expression and provide an explanation of how MeCP2 is able to stimulate H3K27 methylation. While MeCP2 is classically considered to be a transcriptional repressor, it has recently emerged from studies with neurons that it can also function as an activator of transcription for a subset of genes including somatostatin, opioid receptor kappa 1, guanidinoacetate methyltransferase and G protein-regulated inducer of neurite outgrowth 1 (Chahnkour M et al 2008).

Figure 5:
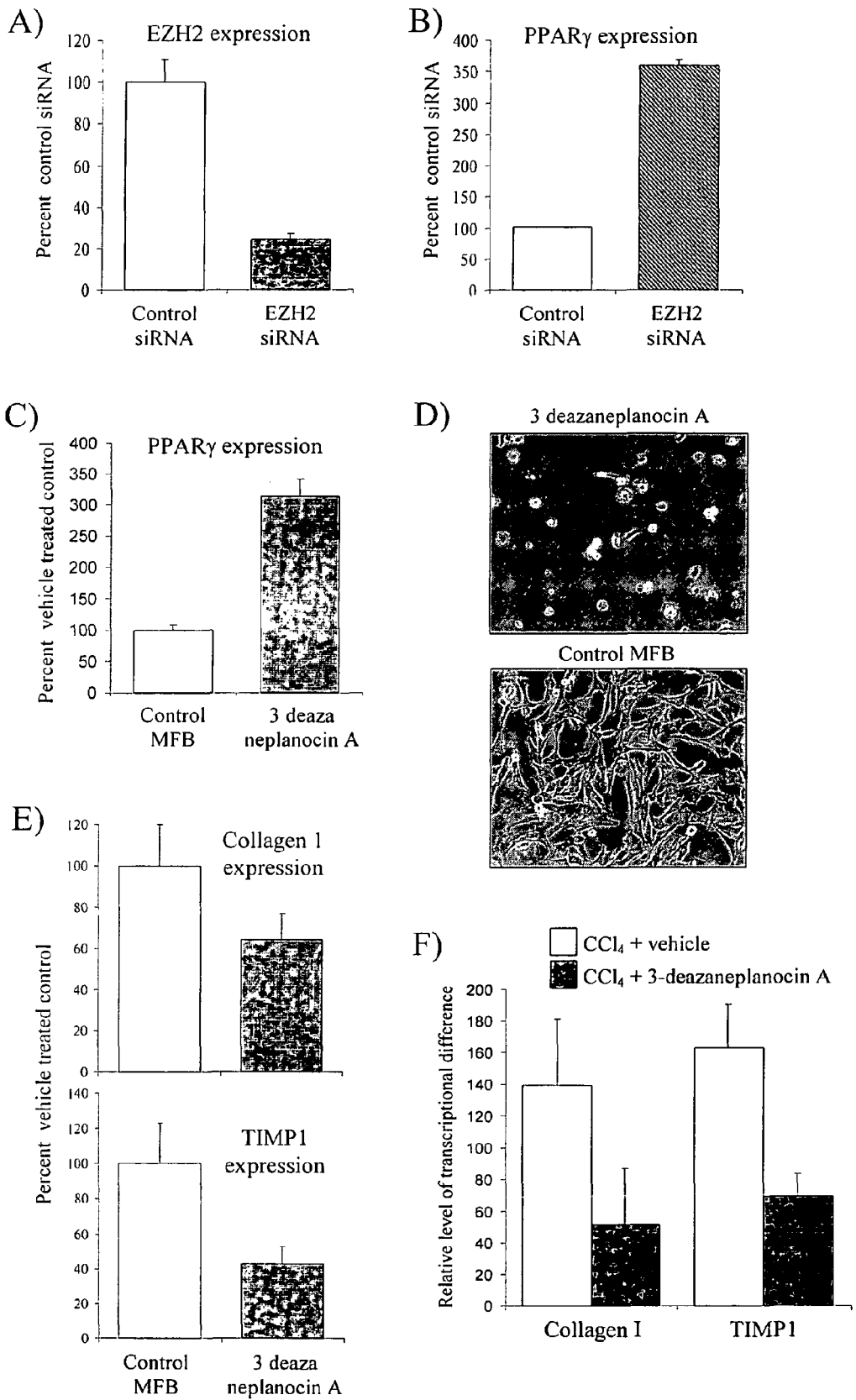
FIG. 5—A.) and B.) 5×10$^6$ rat MFBs were electroporated as outlined "Materials and methods". 2 μgs control siRNA or siRNA designed to target rat EZH2 was used per transfection. Total RNA was prepared from control or rat EZH2 siRNA transfected cells 48 h after the electroporation. First strand cDNA was synthesised which was then utilised as a template in qPCR using primers for specific amplification of EZH2 (in A.) and PPARγ (in B.). C.) Fully differentiated MFBs were treated with 1 μM 3-deazaneplanocin A or vehicle for 72 h at which time total RNA was prepared from control or drug treated cells. First strand cDNA was synthesised which was then utilised as a template in qPCR using primers for specific amplification of PPARγ. D.) Freshly isolated rat HSC were plated out onto plastic in two separate dishes and one dish treated with 1 μM 3-deazaneplanocin A at 12 h following the HSC isolation. Photomicrographs were taken of control and 3-deazaneplanocin A treated dishes after 10 days of culturing. E.) RNA was isolated from a small piece of frozen CCl$_4$ injured C57Bl6 mouse livers from mice pre-treated with 3-deazaneplanocin A or vehicle. First strand cDNA was synthesised which was then utilised as a template in qPCR using primers for specific amplification of mouse collagen I and TIMP1. Each data point is an average of results obtained from 4 mice. Results are expressed as percent control of 3-deazaneplanocin A and olive oil vehicle injected mice (data not included in the graph). 5F-shows that administration of the EZH2 inhibitor to mice during acute liver injury with carbon tetrachloride also suppressed the induction of transcripts for α1 (I) collagen and TIMP-1 which are accurate surrogate markers for the in vivo MTD of hepatic stellate cells and the hepatic wound-healing response.

To provide direct evidence that EZH2 is a regulator of PPARγ gene transcription the inventors employed siRNA-mediated knockdown to achieve an 80% depletion of EZH2 in myofibroblasts (FIG. 5A) and showed that this resulted in elevated expression of PPARγ transcript (FIG. 5B). A similar effect was observed when myofibroblasts were treated with 3 deazaneplanocin A (FIG. 5C) which depletes cells of EZH2 (Tan J et al, 2007). Furthermore, we observed that treatment of freshly isolated quiescent hepatic stellate cells with 3 deazaneplanocin A completely prevented morphological signs of MTD (FIG. 5D) and suppressed the induction of fibrogenic genes al (I) collagen and tissue inhibitor of metalloproteinase-1 (TIMP-1) (FIG. 5E). Administration of the EZH2 inhibitor to mice during acute liver injury with carbon tetrachloride also suppressed the induction of transcripts for al (I) collagen and TIMP-1 which are accurate surrogate markers for the in vivo MTD of hepatic stellate cells and the hepatic wound-healing response (FIG. 5F). EZH2 is therefore a negative regulator of PPARγ transcription in myofibroblasts, but also appears to play a wider regulatory role in promoting MTD and wound-healing. Furthermore, the stimulation of EZH2 expression and subsequent methylation of H3K27 in the downstream exons of the PPARγ gene is identified as a second mechanism through which MeCP2 achieves transcriptional silencing of PPARγ. The combined effect of H3K9 methylation and HP1α binding at the 5' end of the PPARγ gene with H3K27 methylation and PRC1 recruitment in the downstream exons would be to prevent both transcriptional initiation and elongation which reflects the biological importance of suppressing PPARγ expression for MTD and wound-healing.

Figure 9:
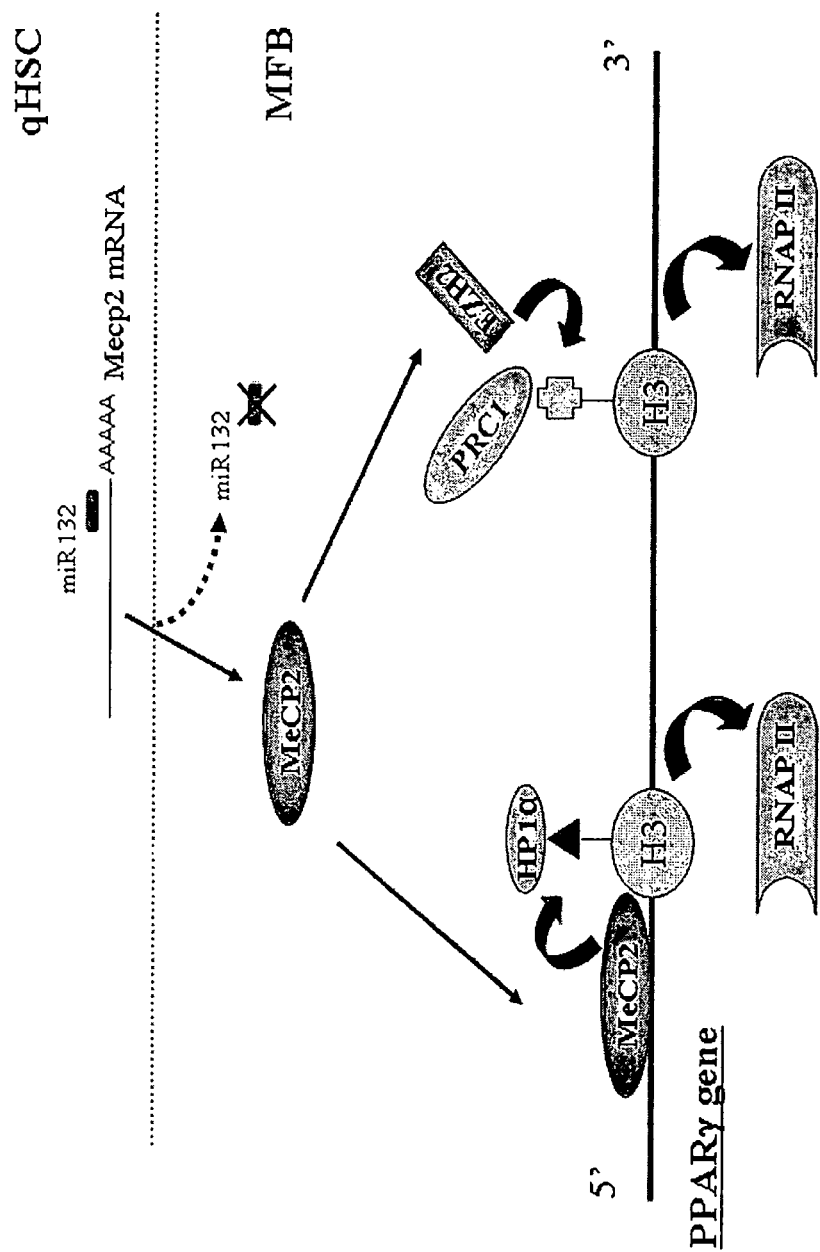
FIG. 9 shows a novel epigenetic relay pathway that is triggered by loss of miR132 expression, leading to subsequent activation of MeCP2, histone lysine methylation events (H3K9 and H3K27) and recruitment of transcriptional repressors such as HP1α.

In summary, the inventors have demonstrated that MTD and in turn wound-healing are subject to tight regulatory control at the epigenetic level involving orchestrators of chromatin modifications associated with gene transcription. More specifically by focusing on the transcriptional silencing of PPARγ during MTD we have discovered a novel epigenetic relay pathway (FIG. 9) that is triggered by loss of miR132 expression, leading to subsequent activation of MeCP2, histone lysine methylation events (H3K9 and H3K27) and recruitment of transcriptional repressors such as HP1α.

Future studies on the role of miR132, MeCP2 and EZH2 are warranted as these factors may provide further insights into the regulation of wound-healing and they may offer interesting targets for the therapeutic correction of inappropriate or unregulated wound-healing and fibrosis. For example, delivery of miR132 or the EZH2 inhibitor 3 deazaneplanocin A to hepatic myofibroblasts using emerging targeting strategies for these cells may be beneficial and can be tested in appropriate animal models (Douglass A et al, 2008, Hagens W I et al 2008). Finally, fibrosis is a common but not a universal consequence of chronic liver injury and infection, for example only 20% of patients with alcoholic liver disease progress to fibrosis. While highly speculative, it is possible that differences in the epigenome of individuals that reflect altered activities in molecules such as miR132, MeCP2 and EZH2 impact on the control of MTD and wound-healing which then determines disease outcome. Future studies in human liver disease with these molecules would therefore be highly appropriate.

Materials and Methods

Chronic $CCl_4$ Liver Injury Model—

Liver fibrosis was generated by 3-week $CCl_4$ treatment of 6 week old Mecp2$^{-/y}$ hemizygote mice or age matched C57Bl6 wild type control littermates. The mice were injected intraperitoneally twice weekly with a mixture of $CCl_4$/olive oil in a 1:1 [vol/vol] ratio at 1 μl per g body weight. Twenty four hours after the final $CCl_4$ administration, animals were sacrificed and liver samples prepared.

Acute $CCL_4$ Liver Injury—

3 deazaneplanocin A was given to two groups of four C57Bl6 mice (15 mg/m² which was calculated to be 0.428 μg of drug per g body weight of a mouse) was given IP 2 hours prior to a single dose of $CCl_4$ ($CCl_4$/olive oil in a 1:1 [vol/vol] ratio at 1 μl per g body weight). Mice were then sacrificed 24 h after the $CCl_4$ injury, bloods taken for assessment of liver enzyme levels and tissues harvested for histological and biochemical analysis.

Cell Isolation and Culture—

Rat HSC were isolated from normal livers of 350-g Sprague-Dawley rats by sequential perfusion with collagenase and Pronase, followed by discontinuous density centrifugation in 11.5% Optiprep (Invitrogen). Mouse HSCs were isolated from C57Bl6 wild type or Mecp2$^{-/y}$ livers as previously described (Oakley F et al 2005). Rat and mouse HSCs were cultured on plastic in Dulbecco's modified Eagle's medium, supplemented with 100 units/ml penicillin, 100 μg/ml streptomycin, 2 mM L-glutamine, and 16% fetal calf serum. Cell cultures were maintained at 37° C. at an atmosphere of 5% $CO_2$.

Immunohistochemistry—

Mouse liver tissue was fixed in 10% formalin in phosphate-buffered saline (PBS), and liver sections stained with Sirius Red as previously described (Wright M C et al 2001).

siRNA Transfection—

Rat MFB were transfected with siRNA designed to silence either rat EZH2 (catalogue numbers s131300 and s131299) or MeCP2 (catalogue numbers s161752 and s161754) or negative control siRNA (catalogue number 4390844, all from Ambion). siRNAs were transfected into 5×10⁶ rat MFB using a square wave electroporator BTX830 (Harvard Apparatus) set at 225V to deliver 3 pulses of 10 ms. Briefly, MFBs were trypsinised, washed once and resuspended in 700 μls serum free media. Cells were mixed with a total of 2 μg siRNA in a 4 mm diameter electroporation cuvette at room temperature and current applied. The cells were allowed to grow for 48 h post transfection when they were harvested and RNA and/or whole cell extracts made.

Micro RNA Detection, Amplification and Transfection—

Micro RNAs were isolated from quiescent rat HSCs and MFBs using miRNeasy mini kit (Qiagen, cat number 217004). Obtained total RNA was reverse transcribed using miScript Reverse Transcription Kit as per manufacturer's instructions. Rat miR132 in the samples was detected using miScript primer assay 218300 (Qiagen, catalogue number MS00000357). To assess the effect of miR132 presence in MFBs, miR132 mimic was purchased from Qiagen (miScript miRNA mimic 219600-S0, catalogue number MSY0000838) and 2 μg were transfected into 5×10⁶ MFBs as outlined for siRNA transfections, except for electroporator settings which were 500V for 1 ms delivered as a single pulse.

SDS-PAGE and Immunoblotting—

Whole cell extracts were prepared, and protein concentration of samples determined using a Bradford DC assay kit (Bio-Rad). Whole cell extracts from samples of interest were then fractionated by electrophoresis through a 9% SDS-polyacrylamide gel. Gels were run at a 100 V for 1.5 hours before transfer onto nitrocellulose. After blockade of nonspecific protein binding, nitrocellulose blots were incubated for 1 hour with primary antibodies diluted in Tris-buffered saline (TBS)/Tween 20 (0.075%) containing 5% bovine serum albumin (BSA). Rabbit polyclonal antibody recognizing MeCP2 (ab-2828, Abcam) was used at 1 μg/ml; EZH2 at 1/500 dilution (Active Motif, catalogue number 39103) and β actin at 1/1000 dilution (Sigma). Following incubation with primary antibodies, blots were washed three times in TBS/Tween 20 before incubation for 1 hour in appropriate HRP-conjugated secondary antibody. After extensive washing in TBS/Tween 20, the blots were processed with distilled water for detection of antigen using the enhanced chemiluminescence system (Amersham Biosciences).

Quantitative Reverse Transcriptase-Polymerase Chain Reaction (RT-PCR)—

Total RNA was purified from isolated cells using the Total RNA purification kit (Qiagen, UK) following the manufacturer's instructions and was used to generate first strand cDNA utilising a random hexamer primer [p(dN)6] and MMLV reverse transcriptase. Primers for rat PPARγ were 5'-atttctgctccacactat-3' (sense) and 5'-gctttatccccacagact-3' (anti-sense); EZH2 were 5'-agtggagtggtgctgaag-3' (sense) and 5'-gccgtccttttcagttg-3' (anti-sense); mouse PPARγ were 5'-aagagctgacccaatggt-3' (sense) and 5'-atggttcttcggaaaaaa-3' (anti-sense); rat β actin were 5'-agagggaaatcgtgcgtgaca-3' (sense) and 5'-acatctgctggaaggtggaca-3' (anti-sense); rat MeCP2 were 5'-ttgaaaaggtgggagaca-3' (sense) and 5'-tgctgct-gcctttggtct-3' (anti-sense); collagen I were 5'-ttc acc tac agc acg ctt gtg-3' (sense) and 5'-gat gac tgt ctt gcc cca agt t-3'

(antisense) and TIMP1 were 5'-gca tgg aca ttt att ctc cac tgt-3' (sense) and 5'-tct cta gga gcc ccg atc tg-3' (antisense). Real-time PCR analysis was performed on an ABI 7500HT sequence detection system. In brief, qPCR reactions comprised of 20 ng of cDNA template, 15 pmoles each of sense and anti-sense oligonucleotide primers and 6.5 µl of Jumpstart SYBR green master mix (Sigma) in a total reaction volume of 13 µl. After the initial 20 sec incubation at 94° C., qPCRs were performed using a 20 sec annealing at 55° C. followed by a 30 sec elongation step at 72° C. and a 5 sec denaturation step at 94° C. After each run, a dissociation curve was performed to ensure that no primer dimers contaminated the quantification and that the product had the expected melting temperature. All PCR reactions were normalized to the internal control and relative level of transcriptional difference calculated using the following equation: [1/(2A)]×100.

3'UTR of MeCP2 Analysis—

Long 3' UTR of MeCP2 mRNA was detected using a number of primer pairs which were designed to specifically detect regions of long 3'UTR that were starting at positions 989 bp (MeCP2 3UTR 1), 1978 bp (MeCP2 3UTR 2), 4063 bp (MeCP2 3UTR 3), 5162 bp (MeCP2 3UTR 4), 6868 bp (MeCP2 3UTR 5) and 8401 bp (MeCP2 3UTR 6) after the stop codon. The primers were: for MeCP2 3UTR 2 were 5'-tcatattggtatatcctttctgtgtt-3' (sense) and 5'-ttgacagttcatg-gcagcag-3' (antisense); MeCP2 3UTR 3 were 5'-ctctgccttg-cagtcaggtt-3'(sense) and 5'-cagcgaaagataccacccata-3' (antisense); MeCP2 3UTR 4 were 5'-attctagggcggatgactga-3' (sense) and 5'-agagagcgggaagaaagagc3' (antisense); MeCP2 3UTR 5 were 5'-atgaccttttgctccttgctc-3'(sense) and 5'-ggaa-gaacagctttgccact-3' (antisense); MeCP2 3UTR 6 were 5'-caatcaataacagacgctcca-3' (sense) and 5'-aagggcaaggaaa-gaagagg-3' (antisense); MeCP2 3UTR 7 were 5'-aaaaa-caaaaggcaatttattaagga-3' (sense) and 5'-aacaaaagacacaaacg-gaca-3' (antisense).

Crosslinked Chromatin Immunoprecipitation (XChIP) Assay—

ChIP assay was carried out using 100 µg crosslinked chromatin prepared from rat HSC or MFB as described previously (Mann J et al 2007). Antibodies used for immunoprecipitation were raised against MeCP2, RNA polymerase II CTD repeat YSPTSPS (phospho S2) and HP1α, all purchased from Abcam. 10 µg of each antibody or appropriate irrelevant antibody control were used in each ChIP reaction. ChIP primers for rat PPARγ gene were promoter or exon specific and the sequences were as follows—PPARγ promoter 5'-ttcccaagtc-ctttccacac-3' (sense) and 5'-gagaggcatggtctctctgg-3' (antisense); PPARγ exon A1 was 5'-aggggactgagtgtgacgac-3' (sense) and 5'-tcacacagtccggtcagaaa-3' (anti-sense); PPARγ exon A2 was 5'-catgctcggagaaagcaaat-3' (sense) and 5'-agtg-gttcacagcttctttcaa-3' (anti-sense); PPARγ exon 1 was 5'-tgaa-gacatcccgttcacaa-3' (sense) and 5'-cgccttctcttcagagtgct-3' (anti-sense); PPARγ exon 2 was 5'-gcacaggtgcgatcaaagta-3' (sense) and 5'-accttgcatccttcacaagc-3' (anti-sense); PPARγ exon 3 was 5'-aagaaccatccgattgaagc-3' (sense) and 5'-gccag-gagcgttacaagatg-3' (anti-sense); PPARγ exon 4 was 5'-gac-cagctgaacccagagtc-3' (sense) and 5'-accccaatgaagagagcaga-3' (anti-sense); PPARγ exon 5 was 5'-ttttcaagggtgccagtttc-3' (sense) and 5'-gaggccagcatggtgtagat-3' (anti-sense); PPARγ exon 6 was 5'-cgaggacatccaagacaacc-3' (sense) and 5'-tcagc-gactgggacttttct-3' (anti-sense); mouse PPARγ promoter was 5'-ctggcgagacaatgtagcaa-3' (sense) and 5'-ttgggagaggtgg-gaataaa-3' (anti-sense). Each PCR reaction was performed in triplicate and the analysis was repeated twice from independent ChIP experiments. A signal intensity value for each sample was calculated from the average of the experiments. Average values of eluates were normalized to average values of inputs.

Native Chromatin Immunoprecipitation (NChIP) Assay—

Native ChIP was carried out as previously described (O'Neill L P et al 2003) using 100 µg native chromatin prepared from rat HSC or MFB. Antibodies raised against dimethylated forms of H3K4, H3K27 and were all purchased from Abcam.

Further Testing

The cardinal role of the smooth muscle myofibroblast in wound-healing is well established, as is the concept that persistence of myofibroblasts in chronic injury leads to a fibrotic response. Myofibroblasts are rare in uninjured tissues but are generated in response to trauma, inflammation or infection by the transdifferentiation of resident cells. In the liver, hepatic myofibroblasts are chiefly generated by transdifferentiation of perisinusoidal hepatic stellate cells (HSC). In the uninjured liver, HSCs are quiescent, retinoid storing cells with an adipogenic phenotype characterised by expression of PPARγ, SREBP1c and adipsin. Upon liver injury, HSCs change phenotype to become a collagen I/III-expressing myofibroblast via a process referred to as myofibroblast transdifferentiation (MTD). In acute liver injury, MTD is a healthy response that ensures wound contraction and formation of a temporary collagen-rich scar. Hepatic myofibroblasts generated in the acute response are soon cleared by apoptosis which enables resolution of wound-healing and regeneration of normal hepatic tissue structure. However, when injury is iterative (such as in the chronic HCV infected liver) myofibroblasts fail to undergo apoptosis and instead expand due to proliferation and progressive rounds of MTD; this leads to expansion and spread of the fibrogenic reaction which if unchecked is the cause of cirrhosis and underlies development of 90% of primary liver cancers. Therefore, any agents that either prevent MTD or induce apoptosis in hepatic myofibroblasts are potential therapeutics for liver fibrosis.

Freshly isolated hepatic stellate cells cultured on plastic in full media spontaneously undergo MTD in a fashion that resembles in vivo events. This process involves morphological changes as well as changes in the expression of hundreds of genes including transcriptional silencing of adipogenic genes and induction of profibrogenic genes such as TIMP1, αSMA, and most importantly collagen 1 and 3. Due to a very defined presentation of morphological changes associated with biochemical change (large upregulation in collagen production) in hepatic stellate cells undergoing MTD, it is possible to monitor progression of MTD over a 7 day period. At the end of 7 days, all quiescent stellate cells in culture would have undergone MTD.

Figure 10A:
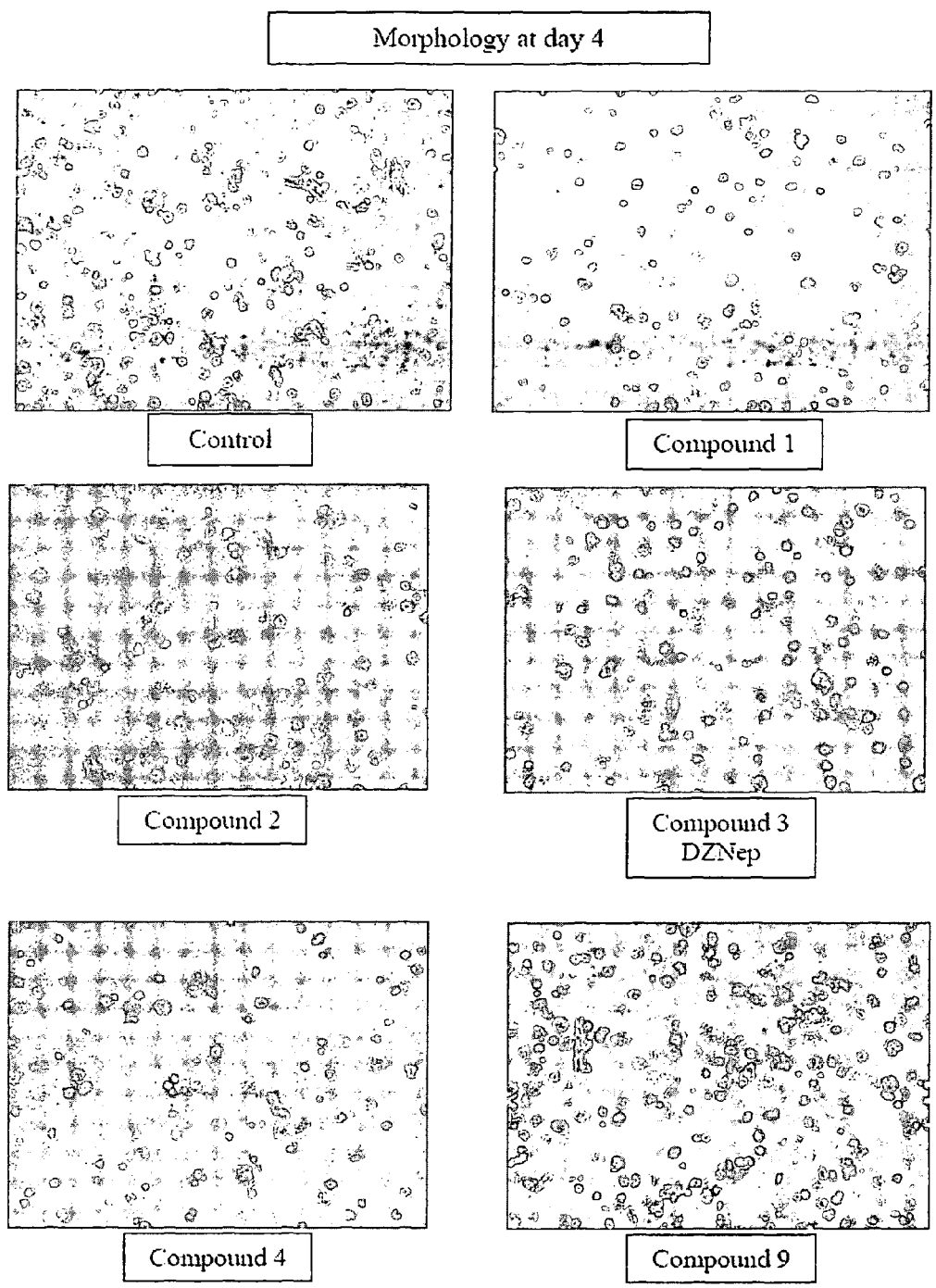
FIGS. 10A and 10B shows the photographs of cells growing in presence of several compounds (Table 1) which were taken on day 4 (early MTD) and day 7 (full MTD). These results show that several drugs of Table 1 hereof prevent/inhibit morphological changes associated with MTD.
Figure 10B:
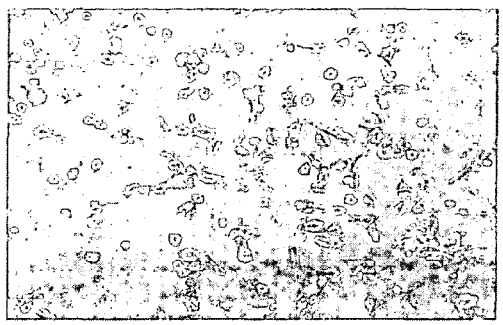
Figure 10B:
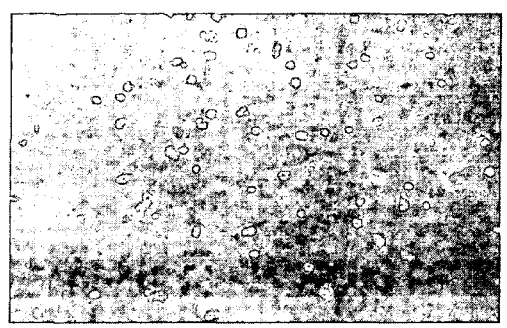
Figure 10B:
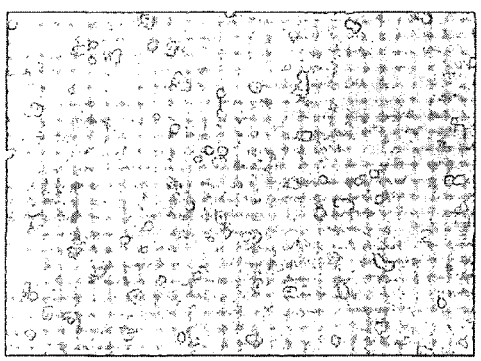
Figure 10B:
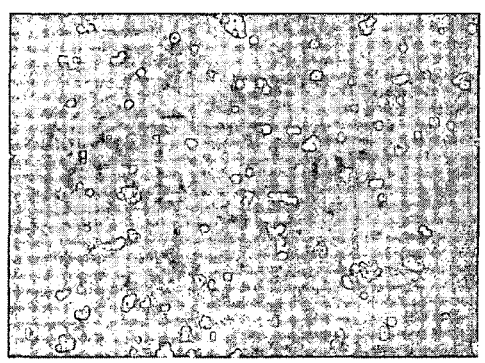
Figure 10B:
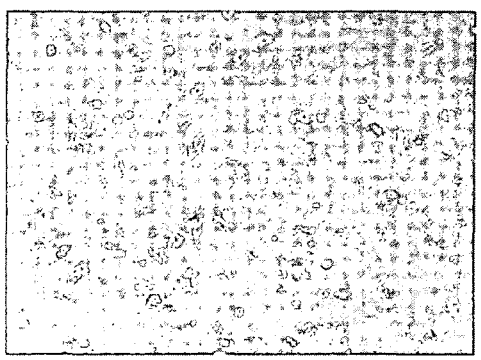
Figure 10B:
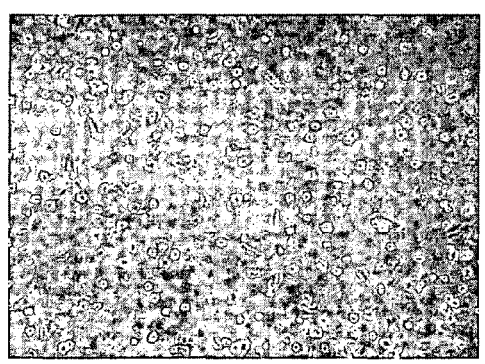
Figure 11:
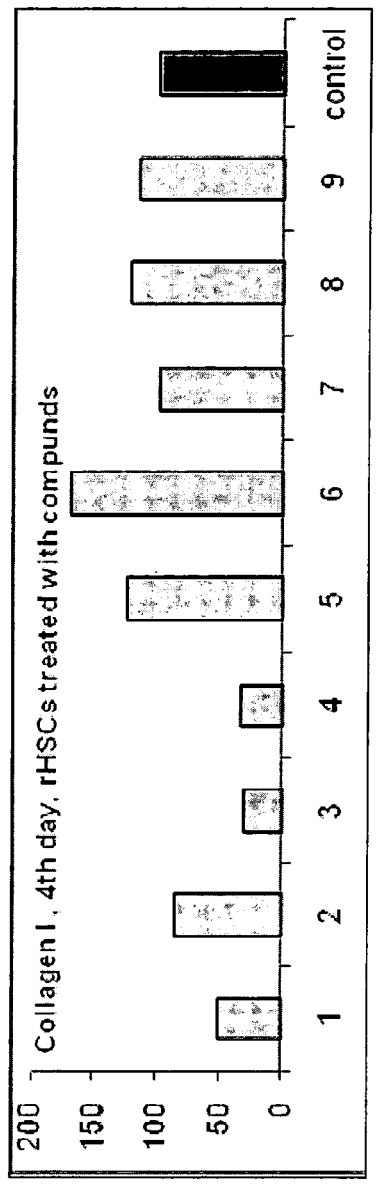
FIG. 11 shows that several drugs of Table 1 hereof inhibit fibrogenic activity of the cells as measured by production of collagen I.
Figure 11:
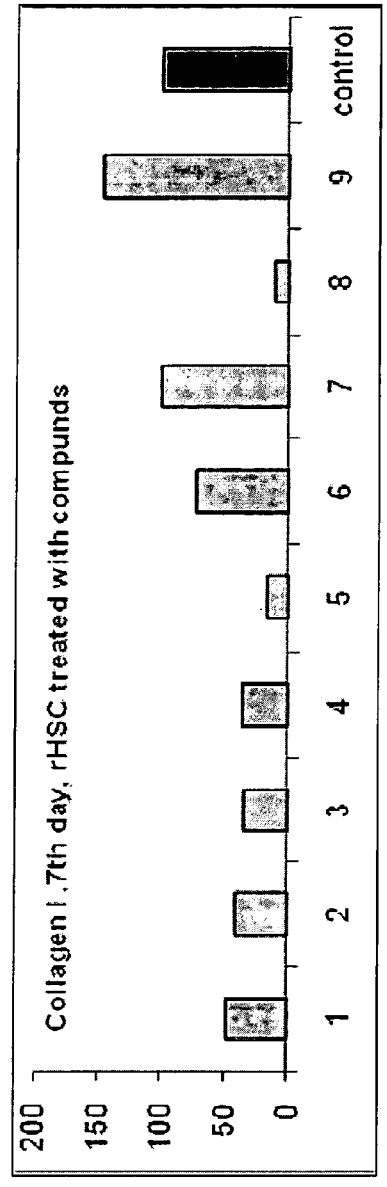

To test derivatives of 3-deazaneplanocin A (Table 1, below) in their ability to halt MTD in hepatic stellate cells, we plated out quiescent, freshly isolated cells onto tissue culture plastic. Photographs of quiescent stellate cells in culture were taken as shown and RNA isolated from some of the cells—this forms the starting point. The cultures were then either left to undergo MTD over 7 days (control cells) or were incubated with 1 µM concentration of drugs 1-9 as set forth in Table 1, hereinbelow. Only one dose of drug was given at the start of culturing which was sufficient to exert effects over a week of cell growth. Photographs of cells growing in presence of various compounds were taken on day 4 (early MTD) and day 7 (full MTD) (FIGS. 10A and B). RNA was also isolated on days 4 and 7. Photographs (Figure show that drugs 1-4 prevent morphological changes associated with MTD, as well as inhibit fibrogenic activity of the cells as measured by production of collagen I (FIG. 11). Compounds 5 and 8 showed significant inhibition at 7 days as evidenced by the results set forth in FIG. 11. Compound 9 is used as a secondary control as it does not inhibit MTD. Compound 3 is the original compound, 3-deazaneplanocin A. Therefore, we have further 3 compounds (1, 2 and 4) that may be effective in vivo treatment of liver fibrosis aside from the originally described one.

TABLE 1

| Compound No. | Structure | MF/MW |
|---|---|---|
| 1 | | $C_{11}H_{13}N_5O_3$ / 263.3 |
| 2 | | $C_{14}H_{18}ClN_5O_3$ / 339.8 |
| 3 | | $C_{12}H_{15}ClN_4O_3$ / 298.7 |
| 4 | | $C_{20}H_{28}N_4O_4$ / 388.5 |
| 5 | 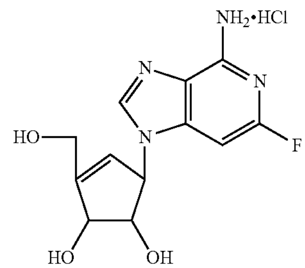 | $C_{12}H_{14}FN_4O_3$ / 316.1 |
| 6 | 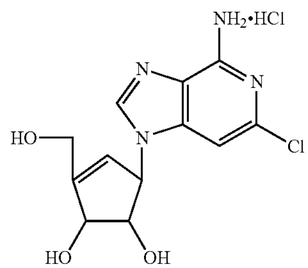 | $C_{12}H_{14}Cl_2N_4O_3$ / 333.2 |
| 7 | 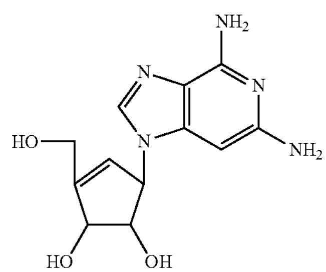 [SMILES: Nc1cc2c(ncn2C2C=C(CO)C(O)C2O)c(N)n1] | $C_{12}H_{15}N_5O_3$ / 277.3 |
| 8 | 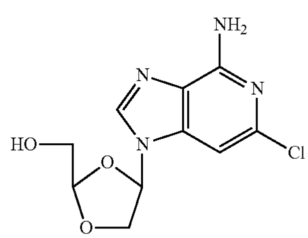 [SMILES: Nc1nc(Cl)cc2c1ncn2C1COC(CO)O1] | $C_{10}H_{11}ClN_4O_3$ / 270.7 |
| 9 | 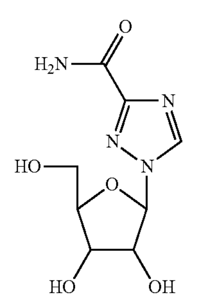 [SMILES: NC(=O)c1ncn(C2OC(CO)C(O)C2O)n1] | $C_8H_{12}N_4O_5$ / 244.2 |

REFERENCES

1. Yavrom S, Chen L, Xiong S, Wang J, Rippe R A, Tsukamoto H. Peroxisome proliferator-activated receptor gamma suppresses proximal alpha1(I) collagen promoter via inhibition of p300-facilitated NF-I binding to DNA in hepatic stellate cells. J Biol. Chem. 2005 Dec. 9; 280(49): 40650-9.

2. Klein M E, Lioy D T, Ma L, Impey S, Mandel G, Goodman R H. Homeostatic regulation of MeCP2 expression by a CREB-induced microRNA. Nat. Neurosci. 2007 December; 10(12): 1513-4.
3. Fuks F, Hurd P J, Deplus R, Kouzarides T. The DNA methyltransferases associate with HP1 and the SUV39H1 histone methyltransferase. Nucleic Acids Res. 2003 May 1; 31(9):2305-12.
4. Kirmizis A, Bartley S M, Kuzmichev A, Margueron R, Reinberg D, Green R, Farnham P J. Silencing of human polycomb target genes is associated with methylation of histone H3 Lys 27. Genes Dev. 2004 Jul. 1; 18(13):1592-605
5. Schotta, G., Lachner, M., Peters, A. H., and Jenuwein, T. (2004) Novartis Found. Symp. 259, 22-47, 163-169
6. Houglum K, Lee K S, Chojkier M. Proliferation of hepatic stellate cells is inhibited by phosphorylation of CREB on serine 133. *J Clin Invest*. 1997 Mar. 15; 99(6):1322-8.
7. Maim J, Oakley F, Akiboye F, Elsharkawy A, Thorne A W, Mann D A. Regulation of myofibroblast transdifferentiation by DNA methylation and MeCP2: implications for wound healing and fibrogenesis. Cell Death Differ. 2007 February; 14(2):275-85.
8. O'Neill L P, Turner B M. Immunoprecipitation of native chromatin: NChIP. Methods. 2003 September; 31(1):76-82.
9. Wright M C, Issa R, Smart D E, Trim N, Murray G I, Primrose J N, Arthur M J, Iredale J P, Mann D A. Gliotoxin stimulates the apoptosis of human and rat hepatic stellate cells and enhances the resolution of liver fibrosis in rats. Gastroenterology. 2001 September; 121(3):685-98.
10. Oakley F, Mann J, Nailard S, Smart D E, Mungalsingh N, Constandinou C, Ali S, Wilson S J, Millward-Sadler H, Iredale J P, Mann D A. Nuclear factor-kappaB1 (p50) limits the inflammatory and fibrogenic responses to chronic injury. Am J Pathol. 2005 March; 166(3):695-708.
11. De Minicis S, Seki E, Uchinami H, Kluwe J, Zhang Y, Brenner D A, Schwabe R F. Gene expression profiles during hepatic stellate cell activation in culture and in vivo. Gastroenterology. 2007 May; 132(5): 1937-46.
12. Hui A Y, Friedman S L. Molecular basis of hepatic fibrosis. Expert Rev Mol. Med. 2003 Feb. 14; 5(5):1-23. Review.
13. Tsukamoto H, She H, Hazra S, Cheng J, Miyahara T. Anti-adipogenic regulation underlies hepatic stellate cell transdifferentiation. J Gastroenterol Hepatol. 2006 October; 21 Suppl 3:S102-5. Review.
14. She H, Xiong S, Hazra S, Tsukamoto H. Adipogenic transcriptional regulation of hepatic stellate cells. J Biol. Chem. 2005 Feb. 11; 280(6):4959-67.
15. Friedman S L. Mechanisms of hepatic fibrogenesis. Gastroenterology. 2008 May; 134(6):1655-69. Review.
16. Iredale J P, Benyon R C, Arthur M J, Ferris W F, Alcolado R, Winwood P J, Clark N, Murphy G. Tissue inhibitor of metalloproteinase-1 messenger RNA expression is enhanced relative to interstitial collagenase messenger RNA in experimental liver injury and fibrosis. Hepatology. 1996 July; 24(1):176-84.
17. Klemm D J, Leitner J W, Watson P, Nesterova A, Reusch J E, Goalstone M L, Draznin B. J Biol. Chem. 2001 Jul. 27; 276(30):28430-5.
18. Hazra S, Xiong S, Wang J, Rippe R A, Krishna V, Chatterjee K, Tsukamoto H. Peroxisome proliferator-activated receptor gamma induces a phenotypic switch from activated to quiescent hepatic stellate cells. J Biol. Chem. 2004 Mar. 19; 279(12):11392-401.
19. Fuks F, Hurd P J, Deplus R, Kouzarides T. The DNA methyltransferases associate with HP1 and the SUV39H1 histone methyltransferase. Nucleic Acids Res. 2003 May 1; 31(9):2305-12.
20. Cheutin T, McNairn A J, Jenuwein T, Gilbert D M, Singh P B, Misteli T. Maintenance of stable heterochromatin domains by dynamic HP1 binding. Science. 2003 Jan. 31; 299(5607):721-5.
21. Francis N J, Kingston R E Woodcock C L. Chromatin compaction by a polycomb group protein complex. Science. 2004 Nov. 26; 306(5701):1574-7.
22. Chahrour M, Jung S Y, Shaw C, Zhou X, Wong S T, Qin J, Zoghbi H Y. MeCP2, a key contributor to neurological disease, activates and represses transcription. Science. 2008 May 30; 320(5880):1224-9.
23. Friedman S L. Hepatic stellate cells: protean, multifunctional, and enigmatic cells of the liver. Physiol Rev. 2008 January; 88(1):125-72. Review.

The invention claimed is:

1. A method of treating or inhibiting fibrogenesis, or treating a fibrotic disease or a secondary disease state or condition thereof comprising administering to a patient in need thereof a compound according to the chemical structure

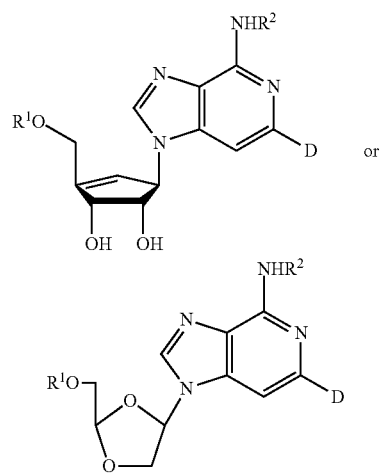

Where $R^1$ is H, an acyl group, a $C_1$-$C_{20}$ alkyl or ether group, an amino acid group (D or L), a phosphate, diphosphate, triphosphate or phosphodiester group;

$R^2$ is H, an acyl group, a $C_1$-$C_{20}$ alkyl or ether group or an amino acid group (D or L); and D is H, F, Cl or Br, or a pharmaceutically acceptable salt thereof, wherein said fibrotic disease is liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery or injection fibrosis and said secondary disease state or condition is cirrhosis, diffuse parenchymal lung disease, post-vasectomy pain syndrome or rheumatoid arthritis.

2. The method according to claim 1 wherein said compound is

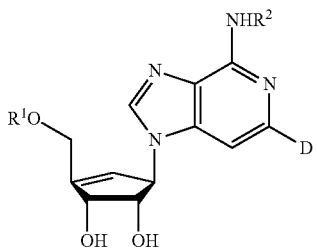

where R¹ and R² are both H; and
D is H or F, or
a pharmaceutically acceptable salt thereof.

3. The method according to claim 1 wherein said compound is

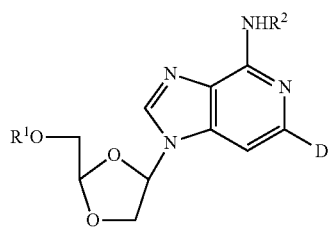

R¹ and R² are both H; and
D is F, Cl or Br or
a pharmaceutically acceptable salt thereof.

4. The method according to claim 1 wherein said fibrotic disease is liver fibrosis, renal fibrosis or lung fibrosis.

5. The method according to claim 1 wherein said fibrotic disease is hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis or nephrogenic systemic fibrosis.

6. The method according to claim 1 wherein said fibrotic disease is macular degeneration or fibrotic complications of surgery or injection fibrosis.

7. The method according to claim 1 wherein said secondary disease state or condition is cirrhosis or diffuse parenchymal lung disease.

8. The method according to claim 1 wherein said secondary disease state or condition is post-vasectomy pain syndrome or rheumatoid arthritis.

9. The method according to claim 2 wherein said fibrotic disease is liver fibrosis, renal fibrosis or lung fibrosis.

10. The method according to claim 2 wherein said fibrotic disease is hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis or nephrogenic systemic fibrosis.

11. The method according to claim 2 wherein said fibrotic disease is macular degeneration or fibrotic complications of surgery or injection fibrosis.

12. The method according to claim 2 wherein said secondary disease state or condition is cirrhosis or diffuse parenchymal lung disease.

13. The method according to claim 2 wherein said secondary disease state or condition is post-vasectomy pain syndrome or rheumatoid arthritis.

14. The method according to claim 3 wherein said fibrotic disease is liver fibrosis, renal fibrosis or lung fibrosis.

15. The method according to claim 3 wherein said fibrotic disease is hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis or nephrogenic systemic fibrosis.

16. The method according to claim 3 wherein said fibrotic disease is macular degeneration or fibrotic complications of surgery or injection fibrosis.

17. The method according to claim 3 wherein said secondary disease state or condition is cirrhosis or diffuse parenchymal lung disease.

18. The method according to claim 3 wherein said secondary disease state or condition is post-vasectomy pain syndrome or rheumatoid arthritis.

\* \* \* \* \*